US008367427B2

(12) United States Patent
Darvari et al.

(10) Patent No.: US 8,367,427 B2
(45) Date of Patent: Feb. 5, 2013

(54) METHODS OF PROCESSING COMPOSITIONS CONTAINING MICROPARTICLES

(75) Inventors: Ramin Darvari, Lexington, MA (US); Adam Lambert, North Canton, OH (US); Julia E. Rashba-Step, Newton, MA (US); Mark X. Yang, Newton, MA (US); Junhong Zhang, Needham, MA (US); Ed O'Connell, Brighton, MA (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 602 days.

(21) Appl. No.: 12/195,092

(22) Filed: Aug. 20, 2008

(65) Prior Publication Data
US 2010/0047248 A1 Feb. 25, 2010

(51) Int. Cl.
*G01N 33/543* (2006.01)
(52) U.S. Cl. ........ 436/518; 435/7.1; 435/7.92; 436/523; 436/524; 436/532
(58) Field of Classification Search ................. None
See application file for complete search history.

(56) References Cited

U.S. PATENT DOCUMENTS

| | | |
|---|---|---|
| 3,737,337 A | 6/1973 | Schnoring et al. |
| 3,891,570 A | 6/1975 | Fukushima et al. |
| 4,389,330 A | 6/1983 | Tice et al. |
| 4,396,560 A | 8/1983 | Stofer |
| 4,416,859 A | 11/1983 | Brown et al. |
| 4,486,315 A | 12/1984 | Teipel |
| 4,530,840 A | 7/1985 | Tice et al. |
| 4,652,441 A | 3/1987 | Okada et al. |
| 4,728,721 A | 3/1988 | Yamamoto et al. |
| 4,732,333 A | 3/1988 | Aria |
| 4,818,542 A | 4/1989 | DeLuca et al. |
| 4,849,228 A | 7/1989 | Yamamoto et al. |
| 4,861,627 A | 8/1989 | Mathiowitz et al. |
| 4,897,268 A | 1/1990 | Tice et al. |
| 4,904,479 A | 2/1990 | Illum et al. |
| 4,917,893 A | 4/1990 | Okada et al. |
| 5,019,400 A | 5/1991 | Gombotz et al. |
| 5,075,109 A | 12/1991 | Tice et al. |
| 5,102,872 A | 4/1992 | Singh et al. |
| 5,149,543 A | 9/1992 | Cohen et al. |
| 5,160,745 A | 11/1992 | DeLuca et al. |
| 5,213,812 A | 5/1993 | Ruiz et al. |
| 5,227,239 A | 7/1993 | Upadhye et al. |
| 5,271,961 A | 12/1993 | Mathiowitz et al. |
| 5,300,464 A | 4/1994 | Rittler |
| 5,330,767 A | 7/1994 | Yamamoto et al. |
| 5,330,768 A | 7/1994 | Park et al. |
| 5,360,610 A | 11/1994 | Tice et al. |
| 5,384,133 A | 1/1995 | Boyes et al. |
| 5,407,609 A | 4/1995 | Tice et al. |
| 5,417,986 A | 5/1995 | Reid et al. |
| 5,422,120 A | 6/1995 | Kim |
| 5,476,663 A | 12/1995 | Okada et al. |
| 5,480,656 A | 1/1996 | Okada et al. |
| 5,482,927 A | 1/1996 | Maniar et al. |
| 5,525,519 A | 6/1996 | Woiszwillo |
| 5,543,158 A | 8/1996 | Gref et al. |
| 5,554,730 A | 9/1996 | Woiszwillo et al. |
| 5,556,642 A | 9/1996 | Kobayashi et al. |
| 5,575,987 A | 11/1996 | Kamei et al. |
| 5,578,709 A | 11/1996 | Woiszwillo et al. |
| 5,599,719 A | 2/1997 | Woiszwillo et al. |
| 5,603,961 A | 2/1997 | Suzuki et al. |
| 5,620,883 A | 4/1997 | Shao et al. |
| 5,631,020 A | 5/1997 | Okada et al. |
| 5,631,021 A | 5/1997 | Okada et al. |
| 5,643,607 A | 7/1997 | Okada et al. |
| 5,650,173 A | 7/1997 | Ramstack et al. |
| 5,654,008 A | 8/1997 | Herbert et al. |
| 5,654,010 A | 8/1997 | Johnson et al. |
| 5,665,428 A | 9/1997 | Cha et al. |
| 5,667,808 A | 9/1997 | Johnson et al. |
| 5,716,640 A | 2/1998 | Kamei et al. |
| 5,851,451 A | 12/1998 | Takechi et al. |

(Continued)

FOREIGN PATENT DOCUMENTS

| | | |
|---|---|---|
| DE | 04312970 | 10/1994 |
| DE | 19812083 | 9/1999 |

(Continued)

OTHER PUBLICATIONS

International Search Report and Written Opinion for corresponding International Application No. PCT/US2009/054550, dated Jun. 18, 2010. International Preliminary Report on Patentability from corresponding International Application No. PCT/US09/54550, dated Nov. 10, 2010.
Ahn et al., "Biodegradable poly(ethylenimine) for plasmid DNA delivery," *J. Control. Rel.*, 80:273-282 (2002).
Al et al., "Nano-encapsulation of furosemide microcrystals for controlled drug release," *J. Control. Rel.*, 86:59-68 (2003).
Atlas of Chromatograms, "Separation of PEG 200 and PEG 2000," *Journal of Chromatographic Science*, 33 (1995).
Ariga et al., "Self-assembly of functional protein multilayers: from planar films to microtemplate encapsulation," pp. 367-391, In: Malmsten (ed.), *Biopolymers at Interfaces*, 2nd ed., Marcel Dekker (2003).

(Continued)

*Primary Examiner* — Gary W Counts
(74) *Attorney, Agent, or Firm* — Marshall, Gerstein & Borun LLP

(57) ABSTRACT

A method for processing multi-phasic dispersions is provided. The method comprises providing a multi-phasic dispersion including dispersed and continuous phases, providing one or more non-solvents comprising an aqueous solution containing at least one multivalent cation, exposing the multi-phasic dispersion to the non-solvent to form a suspension containing one or more liquid phases and the solid microparticles, and removing at least a portion of the resulting one or more liquid phases while retaining at least the microparticles, thereby removing at least a portion of the non-volatile material from the microparticles.

22 Claims, No Drawings

U.S. PATENT DOCUMENTS

| | | | |
|---|---|---|---|
| 5,891,478 A | 4/1999 | Johnson et al. |
| 5,932,248 A | 8/1999 | Chen et al. |
| 5,945,126 A | 8/1999 | Thanoo et al. |
| 5,972,707 A | 10/1999 | Roy et al. |
| 5,981,719 A | 11/1999 | Woiszwillo et al. |
| 5,989,463 A | 11/1999 | Tracy et al. |
| 6,020,175 A | 2/2000 | Onda et al. |
| 6,036,976 A | 3/2000 | Takechi et al. |
| 6,048,550 A | 4/2000 | Chan et al. |
| 6,051,259 A | 4/2000 | Johnson et al. |
| 6,063,910 A | 5/2000 | Debenedetti et al. |
| 6,090,925 A | 7/2000 | Woiszwillo et al. |
| 6,107,084 A | 8/2000 | Onda et al. |
| 6,113,795 A | 9/2000 | Subramaniam et al. |
| 6,120,787 A | 9/2000 | Gustafsson et al. |
| 6,140,475 A | 10/2000 | Margolin et al. |
| 6,153,211 A | 11/2000 | Hubbell et al. |
| 6,242,230 B1 | 6/2001 | Batich et al. |
| 6,265,389 B1 | 7/2001 | Burke |
| 6,268,053 B1 | 7/2001 | Woiszwillo et al. |
| 6,270,795 B1 | 8/2001 | Jones et al. |
| 6,270,802 B1 | 8/2001 | Thanoo et al. |
| 6,312,727 B1 | 11/2001 | Schacht et al. |
| 6,361,798 B1 | 3/2002 | Thanoo et al. |
| 6,395,253 B2 | 5/2002 | Levy et al. |
| 6,395,302 B1 | 5/2002 | Hennink et al. |
| 6,455,074 B1 | 9/2002 | Tracy et al. |
| RE37,872 E | 10/2002 | Franks et al. |
| 6,458,387 B1 | 10/2002 | Scott et al. |
| 6,467,630 B1 | 10/2002 | Zborowski et al. |
| 6,475,995 B1 | 11/2002 | Roy et al. |
| 6,479,146 B1 | 11/2002 | Caruso et al. |
| 6,500,107 B2 | 12/2002 | Brown et al. |
| 6,500,448 B1 | 12/2002 | Johnson et al. |
| 6,506,410 B1 | 1/2003 | Park et al. |
| 6,541,606 B2 | 4/2003 | Margolin et al. |
| 6,569,458 B1 | 5/2003 | Gombotz et al. |
| 6,596,316 B2 | 7/2003 | Lyons et al. |
| 6,616,949 B2 | 9/2003 | Jonsson et al. |
| 6,620,351 B2 | 9/2003 | Gupta et al. |
| RE38,385 E | 1/2004 | Franks et al. |
| 6,699,501 B1 | 3/2004 | Neu et al. |
| 6,713,533 B1 | 3/2004 | Panzner et al. |
| 6,749,866 B2 | 6/2004 | Bernstein et al. |
| 6,814,980 B2 | 11/2004 | Levy et al. |
| 6,830,737 B2 | 12/2004 | Ramstack |
| 6,833,192 B1 | 12/2004 | Caruso et al. |
| 6,861,064 B1 | 3/2005 | Laakso et al. |
| 6,998,051 B2 | 2/2006 | Chattopadhyay et al. |
| 7,374,782 B2 | 5/2008 | Brown et al. |
| 2001/0002261 A1 | 5/2001 | Morrison et al. |
| 2002/0137156 A1 | 9/2002 | Margolin et al. |
| 2002/0146459 A1 | 10/2002 | Levy et al. |
| 2002/0179540 A1 | 12/2002 | Perrut |
| 2002/0187197 A1 | 12/2002 | Caruso et al. |
| 2002/0197325 A1 | 12/2002 | Osborne |
| 2003/0007990 A1 | 1/2003 | Blankenship et al. |
| 2003/0026844 A1 | 2/2003 | Lee et al. |
| 2003/0059474 A1 | 3/2003 | Scott et al. |
| 2003/0064033 A1 | 4/2003 | Brown et al. |
| 2003/0075817 A1 | 4/2003 | Suzuki et al. |
| 2003/0124368 A1 | 7/2003 | Lynn et al. |
| 2003/0129239 A1 | 7/2003 | Goldshtein |
| 2003/0137067 A1 | 7/2003 | Cooper et al. |
| 2003/0157181 A1 | 8/2003 | Panzner et al. |
| 2003/0175239 A1 | 9/2003 | Margolin et al. |
| 2003/0180370 A1 | 9/2003 | Lesniak et al. |
| 2003/0211153 A1 | 11/2003 | Johnson et al. |
| 2003/0219384 A1 | 11/2003 | Donath et al. |
| 2003/0236214 A1 | 12/2003 | Wolff et al. |
| 2004/0013721 A1 | 1/2004 | Antipov et al. |
| 2004/0013738 A1 | 1/2004 | Voigt et al. |
| 2004/0014698 A1 | 1/2004 | Hortelano et al. |
| 2004/0017018 A1 | 1/2004 | Pommersheim |
| 2004/0043076 A1 | 3/2004 | Dulieu et al. |
| 2004/0047979 A1 | 3/2004 | Qiu et al. |
| 2004/0086459 A1 | 5/2004 | Ottoboni et al. |
| 2004/0110898 A1 | 6/2004 | Dreja et al. |
| 2004/0195710 A1 | 10/2004 | Hubbell et al. |
| 2004/0200774 A1 | 10/2004 | Shekunov et al. |
| 2004/0202643 A1 | 10/2004 | Margolin et al. |
| 2004/0209804 A1 | 10/2004 | Govardhan et al. |
| 2004/0219224 A1 | 11/2004 | Yakovlevsky et al. |
| 2004/0241202 A1 | 12/2004 | Chluba et al. |
| 2004/0247624 A1 | 12/2004 | Unger et al. |
| 2004/0258762 A1 | 12/2004 | Boppart et al. |
| 2005/0048127 A1 | 3/2005 | Brown et al. |
| 2005/0142201 A1 | 6/2005 | Rashba-Step et al. |
| 2005/0142205 A1 | 6/2005 | Rashba-Step et al. |
| 2005/0142206 A1 | 6/2005 | Brown et al. |
| 2005/0147687 A1* | 7/2005 | Rashba-Step et al. ........ 424/489 |
| 2005/0170005 A1 | 8/2005 | Rashba-Step et al. |
| 2005/0233945 A1 | 10/2005 | Brown et al. |
| 2005/0247564 A1 | 11/2005 | Volkel et al. |
| 2005/0271732 A1 | 12/2005 | Seeney et al. |
| 2006/0018971 A1 | 1/2006 | Scott et al. |
| 2006/0024240 A1 | 2/2006 | Brown et al. |
| 2006/0024379 A1 | 2/2006 | Brown et al. |
| 2006/0260777 A1 | 11/2006 | Rashba-Step et al. |
| 2007/0092452 A1 | 4/2007 | Rashba-Step et al. |
| 2007/0207210 A1 | 9/2007 | Brown et al. |
| 2007/0258975 A1* | 11/2007 | Hagewiesche et al. .... 424/130.1 |
| 2007/0281031 A1 | 12/2007 | Yang et al. |
| 2009/0017124 A1 | 1/2009 | Brown et al. |

FOREIGN PATENT DOCUMENTS

| | | |
|---|---|---|
| DE | 10157799 | 9/2002 |
| EP | 0223428 | 5/1987 |
| EP | 0248531 | 12/1987 |
| EP | 0377477 | 7/1990 |
| EP | 0647477 | 4/1995 |
| EP | 0809110 | 11/1997 |
| EP | 0972563 | 1/2000 |
| EP | 1060741 | 12/2000 |
| EP | 1116516 | 7/2001 |
| GB | 2334900 | 9/1999 |
| JP | 08245815 | 9/1996 |
| WO | WO-93/14110 | 7/1993 |
| WO | WO-94/18947 | 9/1994 |
| WO | WO-94/20856 | 9/1994 |
| WO | WO-95/00128 | 1/1995 |
| WO | WO-99/47252 | 9/1999 |
| WO | WO-99/47253 | 9/1999 |
| WO | WO-00/03797 | 1/2000 |
| WO | WO-00/28972 | 5/2000 |
| WO | WO-00/41679 | 7/2000 |
| WO | WO-00/77281 | 12/2000 |
| WO | WO-01/51196 | 7/2001 |
| WO | WO-01/64330 | 9/2001 |
| WO | WO-02/09864 | 2/2002 |
| WO | WO-02/09865 | 2/2002 |
| WO | WO-02/17888 | 3/2002 |
| WO | WO-02/074431 | 9/2002 |
| WO | WO-03/000014 | 1/2003 |
| WO | WO-03/015750 | 2/2003 |
| WO | WO-03/030874 | 4/2003 |
| WO | WO-03/043729 | 5/2003 |
| WO | WO-03/087384 | 10/2003 |
| WO | WO-03/090920 | 11/2003 |
| WO | WO-03/097706 | 11/2003 |
| WO | WO-2004/030649 | 4/2004 |
| WO | WO-2004/060920 | 7/2004 |
| WO | WO-2004/062784 | 7/2004 |
| WO | WO-2004/100928 | 11/2004 |
| WO | WO-2005/035088 | 4/2005 |
| WO | WO-2005/051355 | 6/2005 |
| WO | WO-2005/077414 | 8/2005 |
| WO | WO-2005/089727 | 9/2005 |
| WO | WO-2005/112885 | 12/2005 |
| WO | WO-2005/112893 | 12/2005 |
| WO | WO-2005/112894 | 12/2005 |
| WO | WO-2006/012500 A2 | 2/2006 |
| WO | WO-2006/091081 | 8/2006 |
| WO | WO-2008/068455 A1 | 6/2008 |

OTHER PUBLICATIONS

Badin, "Individualite d'une fraction de gammaG-Globulines non precipitables par le zinc a pH 7.3," *Clin. Chim. Acta*, 19:11-18 (1968). [French], summary only.

Badin et al., "Clinical immunochemical study of the serum IgG fraction not precipitated in a zinc-sodium salicylate reagent," *J. Clin. Path.*, 29:984-990 (1976).

Bancherau et al., "Dendritic cells and the control of immunity," *Nature*, 392:245-252 (1998).

Berton et al., "Improved oligonucleotide uptake and stability by a new drug carrier, the supramolecular biovector (SMBV)," *Biochemica Biophysica Acta*, 1355:7-19 (1997).

Bisker-Leib et al., "Uniform microsphere formation from small organic molecules," Transactions, 31st Annual Meeting of the Controlled Release Society, #631A (2004).

Bisker-Lieb et al., "Anti-Factor VII monoclonal antibody microspheres," In: Proceedings of the 2004 American Association of Pharmaceutical Sciences National Biotechnology Conference, p. 76 (2004).

Boussif et al., "A versatile vector for gene and oligonucleotide transfer into cells in culture and in vivo: polyethylenimine," *Proc. Natl. Acad. Sci. USA*, 92:7297-7301 (1995).

Brazeau et al., "In vitro myotoxicity of selected cationic macromolecules used in non-viral gene delivery," *Pharm. Res.*, 15:680-684 (1998).

Brown et al., "PROMAXX microsphere characterization," In: *Proceedings of the Ninth Biennial Respiratory Drug Delivery Conference*, pp. 477-479 (2004).

Brown et al., "Pulmonary delivery of novel insulin microspheres," In: *Proceedings of the Eighth Biennial Respiratory Drug Delivery Conference*, pp. 431-434 (2002).

Bustami et al., "Generation of micro-particles of proteins for aerosol delivery using high pressure modified carbon dioxide," *Pharm. Res.*, 17:1360-1366 (2000).

Byrne et al., "Dendritic cells: making progress with tumour regression?" *Immunol. Cell Biol.*, 80:520-530 (2002).

Chamarthy et al., "A cationic peptide consists of ornithine and histidine repeats augments gene transfer in dendritic cells," *Mol. Immunol.*, 40:483-490 (2003).

Check, "A tragic setback," *Nature*, 420:116-118 (2002).

Chollet et al., "Side-effects of a systemic injection of linear polythylenimine—DNA complexes," *J. Gene Med.*, 41:84-91 (2002).

Chu et al., "Efficiency of cytoplasmic delivery by pH-sensitive liposomes to cells in culture," *Pharm. Res.*, 7:824-834 (1990).

Coombes et al., "Lactic Acid-Stabilised Albumin for Microsphere Formulation and Biomedical Coatings," *Biomaterials*, 22:1-8 (2001).

Couvreur et al., "pH-sensitive liposomes: an intelligent design system for the delivery of antisense oligonucleotides," *J. Liposome Res.*, 7:1-18 (1997).

Crystal, "Transfer of genes to humans: early lessons and obstacles for success," *Science*, 270:404-410 (1995).

Daneshvar, "High-Pressure Phase Equilibria of Poly(ethylene glycol)-Carbon Dioxide Systems," *J. Phys. Chem.*, 94:2124-2128 (1990).

Dokka et al., "Inhibition of endotoxin-induced lung inflammation by interleukin-10 gene transfer in mice," *Am. J. Physiol. Lung Cell Mol. Physiol.*, 279:L872-L877 (2000).

Eliassi et al., "Densities of poly(ethylene glycol) + water mixtures in the 298. 15-328.15 K temperature," *J. Chem. Eng. Data.*, 43:719-721 (1998).

Felgner et al., "Cationic liposome-mediated transfection," *Nature*, 337:387-388 (1989).

Glorioso et al., "Development of herpes simplex virus vectors for gene transfer to the central nervous system," pp. 281-302, In: Wolff (ed.), *Gene Therapeutics: Methods and Applications of Direct Gene Transfer* (1993).

Govardhan et al., "Novel long-acting crystal formulation of human growth hormone," *Pharm. Res.*, 22:1461-1470 (2005).

Hagen et al., "Separation of Oligomers of Polyethylene Glycols by Supercritical Fluid Chromatography," *J. Microcol. Sep.*, 3:27-31 (1991).

Harrison et al., "Effect of Surfactants on the Interfacial Tension Between Supercritical Carbon Dioxide and Polyethylene Glycol," *Langmuir*, 12:2637-2644 (1996).

Hudson et al., "Biodegradable polymer matrices for the sustained exogenous delivery of a biologically active c-myc hammerhead ribozymes," *Int. J. Pharm.*, 136:23-29 (1996).

Hughes et al., "Evaluation of adjuvants that enhance the effectiveness of antisense oligodeoxynucleotides," *Pharm. Res.*, 13:404-410 (1996).

Hwang et al., "Cationic polymers for gene delivery: designs for overcoming barriers to systemic administration," *Curr. Opin. Mol. Ther.*, 3:183-191 (2001).

Jakoby, *Enzyme Purification and Related Techniques. Methods in Enzymology*. vol. XXII. New York: Academic Press (1971).

Johnston et al., "Supercritical Fluid Science and Techology," *ACS Symposium Series 406*, pp. 72-85 (1988).

Kabanov et al., "Water-soluble block polycations as carriers for oligonucleotide delivery," *Bioconjugate Chem.*, 6:639-647 (1995).

Kataoka et al., "Spontaneous formation of polyion complex micelles with narrow distribution from antisense oligonucleotide and cationic block copolymer in physiological saline," *Macromolecules*, 29:8556-8557 (1996).

King, "Supercritical Fluid Extraction of Polymers and Solvents: Utilization of the Solubility Parameter Concept," CPC International, Moffett Technical Center, pp. 707-712.

Kinugasa et al., "Separation of Poly(ethylene glycol)s by Supercritical Fluid Chromatography," Abstract Only.

Kroschwitz (ed.), *Kirk-Othmer Encyclopedia of Chemical Technology*, vol. 23, pp. 452-477, New York: John Wiley and Sons (1997).

Larionova et al., "Encapsulation of proteins in polyelectrolyte microcapsules. Factors regulating the protein release," *Proc. Intl. Symp. Control. Rel. Bioact. Mater.*, 28:1398-1399 (2001).

Leach et al., "Encapsulation of protein nanoparticles into uniform-sized microspheres formed in a spinning oil film," *AAPS PharmSciTech*, 6:E605-E617 (2005).

Leaversuch, "Materials renewable PLA polymer gets 'green light' for packaging uses." pp. 1-4. Retrieved from the Internet in Mar. 2002, <URL: http://www.ptonline.com/articles/200203fa2.html>, Mar. 2002.

Legendre, "Delivery of plasmid DNA into mammalian cell lines using pH-sensitive liposomes: comparison with cationic liposomes," *Pharm. Res.*, 9:1235-1242 (1992).

Loke et al., "Delivery of c-myc antisense phosphorothioate oligodeoxynucleotides to hematopoietic cells in culture by liposome fusion: specific reduction in c-myc protein expression correlates with inhibition of cell growth and DNA synthesis," *Curr. Top. Microbiol. Immunol.*, 141:282-289 (1988).

Lvov et al., "Nanoengineered shells for encapsulation and controlled release," pp. 1-3, NSF Nanoscale Science and Engineering Grantees Conference (Dec. 16-18, 2003).

Mahato et al., "Cationic lipid-based gene delivery systems: pharmaceutical perspectives," *Pharm. Res.*, 14:853-859 (1997).

Meiri et al., "Reversible antisense inhibition of Shaker-like Kv1.1 potassium channel expression impairs associative memory in mouse and rat," *Proc. Natl. Acad. Sci. USA*, 94:4430-4434 (1997).

Middaugh, "Oligonucleotide delivery," In: Mathiowitz (ed.), *Encyclopedia of Controlled Drug Delivery*, vol. 2, pp. 691-697, John Wiley & Sons (1999).

Miller, "Human gene therapy comes of age," *Nature*, 357:455-460 (1992).

Moghimi, "Chemical camouflage of nanospheres with a poorly reactive surface: towards development of stealth and target-specific nanocarriers," *Biochimica et Biophysica Acta*, 1590:131-139 (2000).

Morita et al., "Formation and isolation of spherical fine protein microparticles through lyophilization of protein-poly (ethylene glycol) aqueous mixture," *Pharm. Res.*, 17:1367-1373 (2000).

Oberhouser et al., "Enhancing endosomal exit of nucleic acids using pH-sensitive viral fusion peptides," pp. 247-266, In: Akhtar (ed.), *Delivery Strategies for Antisense Oligonucleotides Therapeutics*, Boca Raton, FL: CRC Press (1995).

Pargaonkar et al., "Controlled release of dexamethasone from microcapsules produced by polyelectrolyte layer by layer nanoassembly," *Pharm. Res.*, 22:826-835 (2005).

Perlaky et al., "Growth inhibition of human tumor cell lines by antisense oligonucleotides designed to inhibit p120 expression," *Anti-Cancer Drug Des.*, 8:3-14 (1993).

Pommersheim et al., "Immobilization of enzymes by multilayer microcapsules," *Macromol. Chem. Phys.*, 195:1557-1567 (1994).

Qiu et al., "Studies on the drug release properties of polysaccharide multilayers encapsulated ibuprofen microparticles," *Langmuir*, 17:5375-5380 (2001).

Radler et al., "Structure of DNA-cationic liposome complexes: DNA intercalation in multilamellar membranes in distinct interhelical packing regimes," *Science*, 275:810-814 (1997).

Rashba-Step et al., "Albumin microspheres as drug delivery vehicle for multiple routes of administration," *Proceedings of the Intl. Symp. Control. Rel. Bioact. Mat.*, vol. 28 (2001).

Rashba-Step et al., "PROMAXX protein matrix micropheres for delivery of alpha-1 antitrypsin via the pulmonary route," *Transactions 31st Annual Meeting Control. Rel. Soc.*, #474 (2004).

Sah et al., "Biodegradable microcapsules prepared by a w/o/w technique: effects of shear force to make a primary w/o emulsion on their morphology and protein release," *J. Microencap.*, 12:59-69 (1995).

Schwartz et al., "Synthetic DNA-compacting peptides derived from human sequence enhance cationic lipid-mediated gene transfer in vitro and in vivo," *Gene Ther.*, 6:282-292 (1999).

Sinha et al., "Biodegradable microspheres or protein delivery" *J. Control. Rel.*, 90:261-280 (2003).

Sukhorukov et al., "Controlling release and permeability properties of militilayer [sic] polyelectrolyte capsules," *Proc. Intl. Symp. Control. Rel. Bioact. Mater.*, 28:1402-1403 (2001).

Sunkara et al., "Supercritical Fluids: Drug Delivery Applications of Supercritical Fluid Technology," Drug Delivery Technology, Retrieved from the Internet on Jul. 13, 2006: URL:http://www.drugdelievervtech.com/cgi.bin/articles.cgi?idArticle=14, Jul. 13, 2006.

Sweeney et al., "Efficient therapeutic gene delivery after systemic administration of a novel polyethylenimine/DNA vector in an orthotopic bladder cancer model," *Cancer Res.*, 63:4017-4020 (2003).

Thierry et al., "Overcoming multidrug resistance in human tumor cells using free and liposomally encapsulated antisense oligodeoxynucleotides," *Biochem. Biophys. Res. Commun.*, 190:952-960 (1993).

Tiourina et al., "Encapsulation of alpha chymotrypsin onto the hollow polyelectrolyte microcapsules," *Proc. Intl. Symp. Control. Rel. Bioact. Mater.*, 28:1400-1401 (2001).

Tiyaboonchai et al., "Formulation and characterization of DNA-polyethylenimine-dextran sulfate nanoparticles," *Eur. J. Pharm. Sci.*, 19:191-202 (2003).

Tomlinson et al., "Controllable gene therapy: pharmaceutics of non-viral gene delivery systems," *J. Control. Rel.*, 39:357-372 (1996).

Vanderkerken et al., "Synthesis and evaluation of poly(ethylene glycol)-polylysine block copolymers as carriers for gene delivery," *J. Bioactive Compatible Polymers*, 15:115-138 (2000).

Vanderlubben et al., "Chitosan microparticles for mucosal vaccination against diphtheria: oral and nasal efficacy studies in mice," *Vaccine*, 21:1400-1408 (2003).

Van Drooge et al., "Incorporation of lipophilic drugs in sugar glasses by lyophilization using a mixture of water and tertiary butyl alcohol as solvent," *J. Pharm. Sci.*, 93:713-725 (2004).

Wittaya-Areekul et al., "Freeze-drying of tert-butanol/water cosolvent systems: a case report on formation of a friable freeze-dried powder of tobramycin sulfate," *J. Pharm. Sci.*, 91:1147-1155 (2002).

Yamakawa et al., "Release behavior of poly(lactic acid-co-glycolic acid) implants containing phosphorothioate oligodeoxynucleotide," *Biol. Pharm. Bull.*, 20:455-459 (1997).

Yang et al., "Crystalline monoclonal antibodies for subcutaneous delivery," *Proc. Natl. Acad. Sci. USA*, 100:6934-6939 (2003).

Yang et al., "Layer by layer construction of novel biofunctional fluorescent microparticles for immunoassay applications," *J. Colloid Interface Sci.*, 234:356-362 (2001).

Yang et al., "Novel fluorescent labels prepared by layer to layer assembly on colloids for biodetection systems," *Mat. Res. Soc. Symp. Proceed.*, 667:G5.5.1-G5.5.6 (2001).

Zahr et al., "Fabrication of core-shell drug nanoparticles for therapeutic delivery," *Polymeric Materials: Science and Engineering*, 93:802-803 (2005).

Zelphati et al "Mechanism of oligonucleotide release from cationic lipids," *Proc. Natl. Acad. Sci. USA*, 100:11493-11498 (1996).

Zhao et al., "Modulation of oligonucleotide-induced immune stimulation by cyclodextrin analogs," *Biochem. Pharmacol.*, 52:1537-1544 (1996).

Price, Centrifugation in Density Gradients, New York: Academic Press (1982). Table of Contents Only.

Ashraf-Khorassani et al., Purification of pharmaceutical excipients with supercritical fluid extraction, Pharm. Dev. Technol., 10:507-16 (2005).

Lossow et al., Particle size and protein content of six fractions of the Sf >20 plasma lipoproteins isolated by density gradient centrifugation, J. Lipid Res., 10:68-76 (1969).

Badin et al., "Methode de dosage des gamma-globulines par precipitation zincique en milieu de force ionique elevee: Comparaison avec l'electrophorese, la precipitation en solution zincique diluee et le relargage au sulfate d'ammonium," Path. et Biol., 11:195-201 (1963). Abstract Only.

Badin et al., "Precipitation des gamma globulines dans un reactif associant le zinc et le salicylate de soude. Nature des precipites. Effets des inhibiteurs de la floculation en fonction de la force ionique. " Bull. Soc. Chem. Biol., 43:387-408 (1961). Abstract Only.

US 5,849,884, 12/1998, Woiszwillo et al. (withdrawn)

\* cited by examiner

METHODS OF PROCESSING COMPOSITIONS CONTAINING MICROPARTICLES

BACKGROUND OF THE INVENTION

1. Technical Field

The present disclosure relates to compositions and formulations containing microparticles and to methods of processing such compositions and formulations.

2. Description of Related Technology

Microparticles, microspheres, and microcapsules, referred to herein collectively as "microparticles," are solid or semi-solid particles having a diameter of less than one millimeter, more preferably less than 100 microns, which can be formed of a variety of materials, including but not limited to various polymers and proteins. Microparticles have been used in many different applications, primarily separations, diagnostics, and drug delivery.

The most well known examples of microparticles used in separations techniques are those which are formed of polymers of either synthetic or protein origin, such as polyacrylamide, hydroxyapatite, or agarose. These polymeric microparticles are commonly used to separate molecules such as proteins based on molecular weight and/or ionic charge, or by interaction with molecules chemically coupled to the microparticles.

In the diagnostic area, spherical beads or particles have been commercially available as a tool for biochemists for many years. For example, microparticles have been derivatized with an enzyme, a substrate for an enzyme, or a labeled antibody, and then interacted with a molecule to be detected, either directly or indirectly. A number of derivatized beads are commercially available with various constituents and sizes.

In the controlled drug delivery area, molecules have been encapsulated within microparticles or incorporated into a matrix to provide controlled release of the molecules. A number of different techniques have been used to make such microparticles from various polymers including phase separation, solvent evaporation, emulsification, and spray drying. Generally, the polymers form the supporting structure of the microparticles, and the drug or molecule of interest is incorporated into the supporting structure. Exemplary polymers used for the formation of microparticles include homopolymers and copolymers of lactic acid and glycolic acid (PLGA), block copolymers, and polyphosphazenes.

U.S. Patent Publication No. 2005/0170005 (the '005 publication) discloses phase separation methods for forming microparticles involving dissolving an active agent in an aqueous and/or aqueous-miscible solvent(s) containing a dissolved phase-separation enhancing agent(s) to form a solution in a single liquid phase. The solution is then subjected to a liquid-solid phase separation to cause the active agent to form solid spherical small particles (i.e., the solid phase) while the phase-separation enhancing agent(s) and solvent(s) comprise the liquid phase. The '005 publication discloses methods of harvesting microparticles including washing solutions and/or dry powders comprising microparticles with liquid media in which the active agent is insoluble and the undesired phase-separation enhancing agent is soluble. Disclosed liquid media include organic solvents and supercritical fluids. Such media can undesirably cause damage to any active agents, particularly proteins such as antibodies, within the microparticles.

The '005 publication further teaches that washing microparticles comprising proteins, such as insulin and hGH, with a liquid medium comprising an aqueous solution containing divalent cations, such as $Zn^{2+}$, causes the protein to form a complex having decreased solubility. The solubility of microparticles comprising such proteins is sufficiently low in the divalent cation solution, but undesirable agglomeration of the particles is frequently observed when such solutions are used to wash the microparticles (as a result of complex formation).

SUMMARY OF THE INVENTION

In one embodiment, the methods for processing multi-phasic dispersions involve providing a composition comprising a plurality of solid microparticles and at least one non-volatile material, providing a non-solvent comprising an aqueous solution containing at least one free multivalent cation, exposing the composition to the non-solvent to form a mixture containing one or more liquid phases and the solid microparticles, and removing at least a portion of the one or more liquid phases while retaining at least the microparticles, thereby removing at least a portion of the non-volatile material from the composition, wherein the non-volatile material is more soluble in the non-solvent than are the microparticles, and wherein the solid microparticles do not comprise human growth hormone (hGH) or insulin.

In an additional embodiment, the methods for processing multi-phasic dispersions involve providing a composition comprising a plurality of solid microparticles and at least one non-volatile material, providing a non-solvent comprising an aqueous solution containing at least uncomplexed $Zn^{2+}$ cations, exposing the composition to the non-solvent to form a mixture containing one or more liquid phases and the solid microparticles, and removing at least a portion of the one or more liquid phases while retaining at least the microparticles, thereby removing at least a portion of the non-volatile material from the composition, wherein the non-volatile material is more soluble in the non-solvent than are the microparticles, and wherein the solid microparticles comprise an antibody.

DETAILED DESCRIPTION

The present disclosure relates to compositions and formulations containing microparticles and to methods of processing such compositions and formulations. In accordance with the methods, microparticles are separated from reaction/incubation media so that the microparticles can be collected and/or incorporated into compositions and formulations suitable for drug delivery, diagnostic, separations, and other applications.

The disclosed methods are advantageous for a number of reasons including but not limited to aqueous solvents can be used to process the microparticles, and thus the structural damage to active agents caused by other harvesting methods which utilize organic solvents and/or supercritical fluids can be avoided. Furthermore, agglomeration of microparticles containing proteins is unexpectedly avoided. Additionally, because organic solvents are not used to remove the polymer(s), the obtained microparticles can be free of (e.g., contain less than 0.50 wt. %, less than 0.25 wt. %, and/or 0 wt. %) organic solvent residues. Furthermore, compositions in the form of multi-phasic dispersions can be processed; as the microparticles can be formed in dispersions, the disclosed methods can facilitate increased manufacturing efficiencies.

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Thus, for example, the reference to a microparticle is a reference to one such microparticle or a plurality of such microparticles, including equivalents thereof known to one skilled in the art. Also, as used herein and in the claims, the terms "at least one" and "one or more" have the same meaning and include one, two, three or more. The following terms, unless otherwise indicated, shall be understood to have the following meanings when used in the context of the present disclosure.

"Dispersion" refers to a mixture of matters having at least one dispersed or discontinuous phase (optionally, being finely divided, such as in the form of solid microparticles) present in a solid or non-solid continuous phase (e.g., fluidic, liquid, aqueous, organic, gaseous). Representative examples of dispersions in accordance with the disclosure include solid in solid, solid in liquid, solid in gas, and the like. A dispersion can be substantially homogenous or non-homogenous. A suspension is a particular dispersion in which the discontinuous solid phase (such as microparticles) can remain stably suspended (substantially free of sedimentation) in the continuous phase for extended periods of time (for example, at least 5 seconds, 10 seconds, or 30 seconds, e.g., minutes, hours, days, weeks, months, or even one year or more). The dispersion is typically free of water-immiscible liquids, but multi-phasic dispersions are also possible. "Multi-phasic dispersions" are dispersions having at least two phases, for example, three or even more phases. In one example, such dispersions may comprise two immiscible solvents or solvent systems in addition to a dispersed phase.

"Microparticle" refers to a solid particulate (including substantially solid or semi-solid, but excluding gel, liquid and gas) having an average geometric particle size (sometimes referred to as diameter) of less than about 1 mm, for example, less than about 200 microns, less than about 100 microns, less than about 10 microns, less than about 1 micron, less than about 100 nm, less than about 10 nm, greater than about 0.1 nm, greater than about 1 nm, and ranges between these values. Thus, suitable ranges for average geometric particle size include about 0.1 nm to about 1 mm, about 1 nm to about 1 mm, about 10 nm to about 1 mm, about 100 nm to about 1 mm, about 1 micron to about 1 mm, about 10 microns to about 1 mm, about 100 microns to about 1 mm, about 200 microns to about 1 mm, about 0.1 nm to about 200 microns, about 1 nm to about 200 microns, about 10 nm to about 200 microns, about 100 nm to about 200 microns, about 1 micron to about 200 microns, about 10 microns to about 200 microns, about 100 microns to about 200 microns, about 0.1 nm to about 100 microns, about 1 nm to about 100 microns, about 10 nm to about 100 microns, about 100 nm to about 100 microns, about 1 micron to about 100 microns, about 10 microns to about 100 microns, about 0.1 nm to about 10 microns, about 1 nm to about 10 microns, about 10 nm to about 10 microns, about 100 nm to about 10 microns, about 1 micron to about 10 microns, about 0.1 nm to about 1 micron, about 1 nm to about 1 micron, about 10 nm to about 1 micron, about 100 nm to about 1 micron, about 0.1 nm to about 100 nm, about 1 nm to about 100 nm, about 10 nm to about 100 nm, about 0.1 nm to about 10 nm, about 1 nm to about 10 nm, and/or about 0.1 nm to about 1 nm. Average geometric particle size can be measured by dynamic light scattering methods (such as photocorrelation spectroscopy, laser diffraction, low-angle laser light scattering (LALLS), medium-angle laser light scattering (MALLS)), light obscuration methods (such as Coulter analysis method), or other methods (such as rheology, light or electron microscopy). Microparticles for pulmonary delivery have an aerodynamic particle size as determined by time of flight measurements or Andersen Cascade Impactor measurements. Microparticles having a spherical shape are sometimes referred to as microspheres and nanospheres. Microparticles having an encapsulated structure are sometimes referred to as microcapsules and nanocapsules. Microparticles can be porous, for example, having one or more internal voids and/or cavities. Other microparticles are non-porous and/or are free of such voids or cavities. Microparticles are formed from, in part or in whole, one or more materials including but not limited to active agents, carriers, polymers, complexing agents, stabilizing agents, excipients, ions, moisture, residual solvents, impurities, by-products, and/or manufacturing-related compounds. Microparticles can be crystalline, amorphous, microcrystalline, nanocrystalline, or a combination thereof.

"Active agent" refers to naturally occurring, recombinant, synthetic, or semi-synthetic materials (e.g., compounds, fermentates, extracts, cellular structures) capable of eliciting, directly or indirectly, one or more physical, chemical, and/or biological effects, in vitro and/or in vivo. The active agent can be capable of preventing, alleviating, treating, and/or curing abnormal and/or pathological conditions of a living body, such as by destroying a parasitic organism, or by limiting the effect of a disease or abnormality by materially altering the physiology of the host or parasite. The active agent can be capable of maintaining, increasing, decreasing, limiting, or destroying a physiological body function. The active agent can be capable of diagnosing a physiological condition or state by an in vitro and/or in vivo test. The active agent can be capable of controlling or protecting an environment or living body by attracting, disabling, inhibiting, killing, modifying, repelling and/or retarding an animal or microorganism. The active agent can be capable of otherwise treating (such as deodorizing, protecting, adorning, grooming) a body. Depending on the effect and/or its application, the active agent can further be referred to as a bioactive agent, a pharmaceutical agent (such as a prophylactic agent, a therapeutic agent), a diagnostic agent, a nutritional supplement, and/or a cosmetic agent, and includes, without limitation, examples such as prodrugs, affinity molecules, synthetic organic molecules, polymers, molecules with a molecular weight of 2 kD or less (such as those having a molecular weight of less than about 1.5 kD, or less than about 1 kD), macromolecules (such as those having a molecular weight of greater than about 2 kD, for example, greater than about 5 kD or between about 2 kD and about 5 kD), proteinaceous compounds, peptides, vitamins, steroids, steroid analogs, lipids, nucleic acids, carbohydrates, precursors thereof, and derivatives thereof. Active agents can be ionic or non-ionic, can be neutral, positively charged, negatively charged, or zwitterionic, and can be used singly or in combination of two or more thereof. Active agents can be water-insoluble or water-soluble. Active agents can have an isoelectric point of 7.0 or greater, but preferably less than 7.0.

"Surface-neutral point" refers to the pH of a solution at which the net surface charge of a microparticle is zero.

"Isoelectric point" refers to the pH of a solution at which the net charge of a molecule is zero.

"Proteinaceous compounds" refer to natural, synthetic, semi-synthetic, or recombinant compounds of or related structurally and/or functionally to proteins, such as those containing or consisting essentially of α-amino acids covalently associated through peptide linkages. Non-limiting proteinaceous compounds include globular proteins (e.g., albumins, globulins, histones), fibrous proteins (e.g., collagens, elastins, keratins), compound proteins (including those containing one or more non-peptide components, e.g., glycoproteins, nucleoproteins, mucoproteins, lipoproteins, metalloproteins), therapeutic proteins, fusion proteins, receptors, antigens (such as synthetic or recombinant antigens), viral surface proteins, hormones and hormone analogs, antibodies (such as monoclonal or polyclonal antibodies), enzymes, Fab fragments, cyclic peptides, linear peptides, and the like. Non-limiting therapeutic proteins include bone morphogenic proteins, drug resistance proteins, toxoids, erythropoietins, proteins of the blood clotting cascade (e.g., Factor VII, Factor VIII, Factor IX, et al.), subtilisin, ovalbumin, alpha-1-antitrypsin (AAT), DNase, superoxide dismutase (SOD), lysozymes, ribonucleases, hyaluronidase, collagenase, human growth hormone (hGH), erythropoietin, insulin, insulin-like growth factors, interferons, glatiramer, granulocyte-macrophage colony-stimulating factor, granulocyte colony-stimulating factor, desmopressin, leutinizing hormone release hormone (LHRH) agonists (e.g., leuprolide, goserelin, buserelin, gonadorelin, histrelin, nafarelin, deslorelin, fertirelin, triptorelin), LHRH antagonists, vasopressin, cyclosporine, calcitonin, parathyroid hormone, parathyroid hormone peptides, glucogen-like peptides, and analogs thereof. Proteinaceous compounds may be neutral, positively charged, negatively charged, or zwitterionic, and may be used singly or in combination of two or more thereof.

"Nucleic acids" refer to natural, synthetic, semi-synthetic, or recombinant compounds formed at least in part from two or more of the same or different nucleotides, and may be single-stranded or double-stranded. Non-limiting examples of nucleic acids include oligonucleotides (such as those having 20 or less base pairs, e.g., sense, anti-sense, or missense), aptamers, polynucleotides (e.g., sense, anti-sense, or missense), DNA (e.g., sense, anti-sense, or missense), RNA (e.g., sense, anti-sense, or missense), siRNA, nucleotide acid constructs, single-stranded or double-stranded segments thereof, as well as precursors and derivatives thereof (e.g., glycosylated, hyperglycosylated, PEGylated, FITC-labeled, nucleosides, salts thereof). Nucleic acids may be neutral, positively charged, negatively charged, or zwitterionic, and may be used singly or in combination of two or more thereof.

"Macromolecule" refers to a material capable of providing a three-dimensional (e.g., tertiary and/or quaternary) structure, and includes carriers and certain active agents of the present disclosure. Macromolecules typically have a molecular weight of 2 kD or greater, for example, greater than 5 kD or between 2 kD and 5 kD. Non-limiting macromolecules used to form the microparticles include, inter alia, polymers, copolymers, proteins (e.g., enzymes, recombinant proteins, albumins such as human serum albumin, monoclonal antibodies, polyclonal antibodies, proteinaceous compounds), peptides, lipids, carbohydrates (e.g., monosaccharides, disaccharides, polysaccharides), nucleic acids, vectors (e.g., viruses, viral particles), and complexes and conjugates thereof (e.g., covalent and/or non-covalent associations between two macromolecules such as carbohydrate-protein complexes or conjugates, or between an active agent and a macromolecule such as hapten-protein complexes or conjugates). Macromolecules may be neutral, positively charged, negatively charged, or zwitterionic, and may be used singly or in combination of two or more thereof.

"Carrier" refers to a compound, typically a macromolecule, having a primary function to provide a three-dimensional structure (including tertiary and/or quaternary structure) to the microspheres. The carrier may be unassociated or associated with the active agent (such as conjugates or complexes thereof) in forming microparticles as described above. The carrier may further provide other functions, such as being an active agent, modifying a release profile of the active agent from the microparticle, and/or imparting one or more particular properties to the microparticle (such as contribute at least in part to the net surface charge). In one example, the carrier is a protein (e.g., an albumin such as human serum albumin) having a molecular weight of 1500 Daltons or greater.

"Polymer" or "polymeric" refers to a natural, recombinant, synthetic, or semi-synthetic molecule having in at least one main chain, branch, or ring structure two or more repeating monomer units. Polymers broadly include dimers, trimers, tetramers, oligomers, higher molecular weight polymers, adducts, homopolymers, random copolymers, pseudo-copolymers, statistical copolymers, alternating copolymers, periodic copolymers, bipolymers, terpolymers, quaterpolymers, other forms of copolymers, substituted derivatives thereof, and mixtures thereof. In one aspect, the terms polymer and polymeric refer to molecules having 10 or more repeating monomer units. Polymers can be linear, branched, block, graft, monodisperse, polydisperse, regular, irregular, tactic, isotactic, syndiotactic, stereoregular, atactic, stereoblock, single-strand, double-strand, star, comb, dendritic, and/or ionomeric, can be ionic or non-ionic, can be neutral, positively charged, negatively charged, or zwitterionic, and can be used singly or in combination of two or more thereof.

"Spherical" refers to a geometric shape that is at least "substantially spherical." "Substantially spherical" means that the ratio of the longest length (i.e., one between two points on the perimeter and passes the geometric center of the shape) to the shortest length on any cross-section that passes through the geometric center is less than about 1.5, such as less than about 1.33, or less than about 1.25. Thus, spherical does not require a line of symmetry. Further, the microparticles can have surface texturing (such as continuous or discrete lines, islands, lattice, indentations, channel openings, protuberances that are small in scale when compared to the overall size of the microparticles) and still be considered spherical. Surface contact between microparticles is minimized when the microparticles are spherical, and thus undesirable agglomeration of the microparticles is typically minimized. In comparison, microparticles that are aspherical crystals or flakes typically display observable agglomeration through ionic and/or non-ionic interactions at relatively large flat surfaces.

"Solid" refers to a state that includes at least substantially solid and/or semi-solid, but excludes liquid and gas.

"Ambient temperature" refers to a temperature of around room temperature, typically in a range of about 20° C. to about 40° C., for example, about 20° C. to about 25° C.

"Formed from" and "formed of" denote open language. As such, it is intended that a composition formed from or formed of a list of recited components be a composition comprising at least these recited components, and can further include other non-recited components during formulation of the composition and/or in the final obtained product.

Unless otherwise expressly specified, all of the numerical ranges, amounts, values and percentages such as those for quantities of materials, times, temperatures, reaction conditions, ratios of amounts, values for molecular weight (whether number average molecular weight $M_n$ or weight average molecular weight $M_w$), and others disclosed herein should be understood as modified in all instances by the term "about," if about is not expressly used in combination with said ranges, amounts, values, and percentages herein. Accordingly, unless indicated to the contrary, the numerical parameters set forth in the present disclosure and attached claims are approximations that can vary. At the very least, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, is inherently somewhat uncertain because of the standard deviation found in its respective testing measurement. Furthermore, when numerical ranges of varying scope are set forth herein, it is contemplated that any combination of these values inclusive of the recited values can be used in accordance with the teachings of the disclosure.

Examples provided herein, including those following "such as" and "e.g.," are considered as illustrative only of various aspects and features of the present disclosure and embodiments thereof, and thus should not alter the scope of any of the referenced terms or phrases. Any suitable equivalents, alternatives, and modifications thereof (including materials, substances, constructions, compositions, formulations, means, methods, conditions, etc.) known and/or available to one skilled in the art can be used or carried out in place of or in combination with those disclosed herein, and are considered to fall within the scope of the present disclosure. Throughout the present disclosure in its entirety, any and all of the one, two, or more features and aspects disclosed herein, explicitly or implicitly, following terms "example", "examples", "such as", "e.g.", and the likes thereof may be practiced in any combinations of two, three, or more thereof (including their equivalents, alternatives, and modifications), whenever and wherever appropriate as understood by one of ordinary skill in the art. Therefore, specific details disclosed herein are not to be interpreted as limiting, but merely as a basis for the claims and as a representative basis for teaching one skilled in the art to variously employ aspects and features of the present disclosure in virtually any appropriate manner as understood by one of ordinary skill in the art.

Microparticles

Non-limiting microparticles, materials and methods for fabricating microparticles, compositions and formulations containing microparticles, and utilities of such microparticles, compositions, and formulations include those disclosed in U.S. Pat. Nos. 5,525,519, 5,554,730, 5,578,709, 5,599,719, 5,981,719, 6,090,925, 6,268,053, and 6,458, 387, U.S. Publication Nos. 20030059474, 20030064033, 20040043077, 20050048127, 20050142201, 20050142205, 20050142206, 20050147687, 20050170005, 20050233945, 20060018971, 20060024240, 20060024379, 20060260777, 20070092452, 20070207210, and 20070281031, the disclosures of which are herein incorporated by reference in their entirety. Microparticles can have a generally uniform size distribution, such as a monodisperse size distribution, or a polydisperse size distribution, and a generally uniform shape, such as being substantially spherical. One or more characteristics of the microparticles can be adjusted during fabrication by manipulating one or more variables such as, but not limited to, selection of ingredients or combination thereof, concentrations of different ingredients, reaction temperature, reaction time, and/or pH if reaction is taken place in aqueous solution.

Microparticles are suitable for delivering, in vivo, ex vivo, and/or in vitro, one active agent or a combination of two or more active agents with rapid and/or controlled release profiles, and are useful for a wide variety of therapeutic, pharmaceutical, diagnostic, medical, medicinal, cosmetic, nutritional, biocidic, separational, industrial, commercial, and research applications, such as drug delivery, vaccination, gene therapy and histopathological or in vivo tissue or tumor imaging. Microparticles can be formulated for oral, parenteral, mucosal; ophthalmic; intravenous, subcutaneous, subdermal, intradermal, intra-articular, intramuscular, pulmonary (including oral and nasal inhalations), and/or topical administrations to a subject. Intravenous administration includes catheterization and angioplasty.

The microparticles typically contain one or more macromolecules. The one or more macromolecules (typically, one or more bioactive macromolecules and/or one or more carrier macromolecules) may comprise at least 1%, 5%, 10%, 20%, 30%, 40%, 50%, 60%, 70%, 80%, 90%, 95%, or 98%, and up to 100%, or less than 100%, by weight and/or volume of the microparticle, or be present in a range between any two of such values. It will be understood by those skilled in the art that the macromolecule can be a portion (e.g., fragment, segment, subunit) of another larger macromolecule. It will be further understood that macromolecules include affinity molecules, which can be, for example, the receptor or ligand portions of a receptor-ligand interaction. Non-limiting examples of ligands include viruses, bacteria, polysaccharides, or toxins that act as antigens to generate immune responses when administered to an animal and cause the production of antibodies.

One or more ingredients other than the macromolecules described above and the active agents described below including but not limited to polymers, complexing agents, stabilizing agents, excipients, ions, moisture, residual solvents, impurities, by-products, may be present in the microparticle at a quantity of 50% or less, 30% or less, 20% or less, 10% or less, 5% or less, or 2% or less, or greater than 0%, by weight and/or volume of the microparticle, or in a range between any two of such values. Additionally, any ingredients present in the reaction/incubation medium (e.g., such as non-volatile materials) during the formation of the microparticles can be substantially removed from and thus absent in the resulting microparticles. Immediately or at a later stage following their formation (which may or may not be in-situ), the microparticles may be dispersed (e.g., as colloids or suspensions) in a continuous solid phase (e.g., a frozen solid comprising the dispersion) or in a non-solid phase (e.g., a flowable medium, such as the reaction/incubation medium in which the microparticles are formed, or a washing medium).

The microparticles may have a density substantially the same as or different from (such as greater than or less than) that of the continuous phase (measured at the same temperature, such as ambient temperature). Densities of the microparticles, and the continuous phase equal their respective weight divided by their respective volume. The microparticles may have a density less than, equal to, or greater than values such as $0.5 \text{ g/cm}^3$, $0.8 \text{ g/cm}^3$, $0.95 \text{ g/cm}^3$, $1.0 \text{ g/cm}^3$, $1.05 \text{ g/cm}^3$, $1.1 \text{ g/cm}^3$, $1.3 \text{ g/cm}^3$, $1.35 \text{ g/cm}^3$, $1.5 \text{ g/cm}^3$, and $1.9 \text{ g/cm}^3$, or in a range between any two of such values, such as between $1.0 \text{ g/cm}^3$ and $1.5 \text{ g/cm}^3$ or between $1.2 \text{ g/cm}^3$ and $1.5 \text{ g/cm}^3$. Density of the microparticles may be measured by helium pycnometry at ambient temperature, by density-gradient techniques (e.g., using centrifugation or ultracentrifugation) using suitable gradient medium (e.g., salts of alkali metals such as NaCl, NaBr, NaI, KBr, CsF, CsCl, CsBr, cesium sulfate, cesium acetate, cesium trifluoroacetate, RbCl, and potassium tartrate; neutral, water-soluble molecules such as sucrose with optional addition of glucose, glycerol, or mineral oil; hydrophilic macromolecules such as dextran, sucrose-epichlorohydrin copolymer, and bovine serum albumin; other synthetic molecules such as sodium or methyl glucamine salts of triiodobenzoic acid and of metrizoic acid, and metrizamide), and other known methods. Standard methods involving density-gradient techniques include ASTM D1505-03, ASTM D1505-98, and ISO 1183-2.

Active Agents

One or more active agents are typically covalently and/or non-covalently associated with, and/or entrapped by, at least a portion (e.g., the center or core, one or more specifically or randomly distributed compartments, inner and/or outer surfaces) of the microparticle. For example, the one or more active agents may be covalently and/or non-covalently associated with, and/or entrapped by, at least a portion or substantially all of one or more macromolecules (e.g., bioactive macromolecules and/or carrier macromolecules) and/or one or more other ingredients (e.g., with one or more polymers, as complexes or conjugates thereof). Alternatively, the macromolecule itself can comprise an active agent. In both instances, the microparticles can comprise a bioactive macromolecule on an outer surface thereof.

The active agent may be a pharmaceutical agent. Depending on its effect and/or application, the pharmaceutical agent includes, without limitation, adjuvants, adrenergic agents, adrenergic blocking agents, adrenocorticoids, adrenolytics, adrenomimetics, alkaloids, alkylating agents, allosteric inhibitors, anabolic steroids, analeptics, analgesics, anesthetics, anorexiants, antacids, anti-allergic agents, antiangiogenesis agents, anti-arrhythmic agents, anti-bacterial agents, antibiotics, antibodies, anticancer agents such as paclitaxel and derivative compounds, anticholinergic agents, anticholinesterases, anticoagulants, anticonvulsants, antidementia agents, antidepressants, antidiabetic agents, antidiarrheals, antidotes, antiepileptics, antifolics, antifungals, antigens, antihelmintics, antihistamines, antihyperlipidemics, antihypertensive agents, anti-infective agents, anti-inflammatory agents, antimalarials, antimetabolites, antimuscarinic agents, antimycobacterial agents, antineoplastic agents, antiosteoporosis agents, antipathogen agents, antiprotozoal agents, adhesion molecules, antipyretics, antirheumatic agents, antiseptics, antithyroid agents, antiulcer agents, antiviral agents, anxiolytic sedatives, astringents, beta-adrenoceptor blocking agents, biocides, blood clotting factors, calcitonin, cardiotonics, chemotherapeutics, cholesterol lowering agents, cofactors, corticosteroids, cough suppressants, cytokines, diuretics, dopaminergics, estrogen receptor modulators, enzymes and cofactors thereof, enzyme inhibitors, growth differentiation factors, growth factors, hematological agents, hematopoietics, hemoglobin modifiers, hemostatics, hormones and hormone analogs, hypnotics, hypotensive diuretics, immunological agents, immunostimulants, immunosuppressants, inhibitors, ligands, lipid regulating agents, lymphokines, muscarinics, muscle relaxants, neural blocking agents, neurotropic agents, parasympathomimetics, parathyroid hormone, promoters, prostaglandins, psychotherapeutic agents, psychotropic agents, radio-pharmaceuticals, receptors, sedatives, sex hormones, sterilants, stimulants, thrombopoietics, trophic factors, sympathomimetics, thyroid agents, vaccines, vasodilators, vitamins, xanthines, as well as conjugates, complexes, precursors, and metabolites thereof. The active agent may be used individually or in combinations of two or more thereof. In one example, the active agent is a prophylactic and/or therapeutic agent that includes, but is not limited to, peptides, carbohydrates, nucleic acids, other compounds, precursors and derivatives thereof, and combinations of two or more thereof. In one aspect, the active agent is a pharmaceutical agent that is conventionally referred to as a small molecule.

The active agent may be a bioactive active agent, for example, a bioactive macromolecule, such as a protein (including the proteinaceous compounds described above), a polypeptide, a carbohydrate, a polynucleotide, a vector (e.g., a virus or viral particle), or a nucleic acid, or a combination of two or more thereof. The macromolecule can be natural or synthetic. Exemplary proteins include monoclonal antibodies, polyclonal antibodies. The protein can also be any known therapeutic proteins isolated from natural sources or produced by synthetic or recombinant methods. Examples of therapeutic proteins include, but are not limited to, proteins of the blood clotting cascade (e.g., Factor VII, Factor VIII, Factor IX, et al.), subtilisin, ovalbumin, alpha-1-antitrypsin (AAT), DNase, superoxide dismutase (SOD), lysozyme, ribonuclease, hyaluronidase, collagenase, growth hormone, erythropoietin, insulin-like growth factors or their analogs, interferons, glatiramer, granulocyte-macrophage colony-stimulating factor, granulocyte colony-stimulating factor, antibodies, PEGylated proteins, glycosylated or hyperglycosylated proteins, desmopressin, LHRH agonists such as: leuprolide, goserelin, nafarelin, buserelin; LHRH antagonists, vasopressin, cyclosporine, calcitonin, parathyroid hormone, parathyroid hormone peptides and insulin.

The active agent may be a cosmetic agent. Non-limiting examples of cosmetic agents include emollients, humectants, free radical inhibitors, anti-inflammatory agents, vitamins, depigmenting agents, anti-acne agents, antiseborrhoeics, keratolytics, slimming agents, skin coloring agents, and sunscreen agents. Non-limiting compounds useful as cosmetic agents include linoleic acid, retinol, retinoic acid, ascorbic acid alkyl esters, polyunsaturated fatty acids, nicotinic esters, tocopherol nicotinate, unsaponifiables of rice, soybean or shea, ceramides, hydroxy acids such as glycolic acid, selenium derivatives, antioxidants, beta-carotene, gamma-orizanol, and stearyl glycerate. The cosmetic agents may be commercially available and/or prepared by known techniques. As above, the various active agents may be used individually or in combinations of two or more thereof.

The active agent may be a nutritional supplement. Non-limiting examples of nutritional supplements include proteins, carbohydrates, water-soluble vitamins (e.g., vitamin C, B-complex vitamins, and the like), fat-soluble vitamins (e.g., vitamins A, D, E, K, and the like), and herbal extracts. The nutritional supplements may be commercially available and/or prepared by known techniques. As above, the various active agents may be used individually or in combinations of two or more thereof.

The active agent may be a compound having a molecular weight of 2 kDa or less. Non-limiting examples of such compounds include steroids, beta-agonists, anti-microbial agents, antifungal agents, taxanes (antimitotic and antimicrotubule agents), amino acids, aliphatic compounds, aromatic compounds, and urea compounds. Active agents conventionally known as small molecules (or small organic molecules) are representative active agents having a molecular weight of 2 kDa or less.

The active agent may also be a diagnostic agent. Non-limiting diagnostic agents include x-ray imaging agents and contrast media. Non-limiting examples of x-ray imaging agents include ethyl 3,5-diacetamido-2,4,6-triiodobenzoate (WIN-8883, ethyl ester of diatrazoic acid); 6-ethoxy-6-oxo-hexyl-3,5-bis(acetamido)-2,4,6-triiodobenzoate (WIN 67722); ethyl-2-(3,5-bis(acetamido)-2,4,6-triiodobenzoyloxy)-butyrate (WIN 16318); ethyl diatrizoxyacetate (WIN 12901); ethyl 2-(3,5-bis(acetamido)-2,4,6-triiodobenzoyloxy)propionate (WIN 16923); N-ethyl 2-(3,5-bis(acetamido)-2,4,6-triiodobenzoyloxy-acetamide (WIN 65312); isopropyl 2-(3,5-bis(acetamido)-2,4,6-triiodobenzoyloxy) acetamide (WIN 12855); diethyl 2-(3,5-bis(acetamido)-2,4, 6-triiodobenzoyloxymalonate (WIN 67721); ethyl 2-(3,5-bis (acetamido)-2,4,6-triiodobenzoyloxy)phenyl-acetate (WIN 67585); propanedioic acid, [[3,5-bis(acetylamino)-2,4,5-triodobenzoyl]oxy]bis(1-methyl)ester (WIN 68165); and benzoic acid, 3,5-bis(acetylamino)-2,4,6-triodo-4-(ethyl-3-ethoxy-2-butenoate)ester (WIN 68209). Preferred contrast agents desirably disintegrate relatively rapidly under physiological conditions, thus minimizing any particle associated inflammatory response. Disintegration may result from enzymatic hydrolysis, solubilization of carboxylic acids at physiological pH, or other mechanisms. Thus, poorly soluble iodinated carboxylic acids such as iodipamide, diatrizoic acid, and metrizoic acid, along with hydrolytically labile iodinated species such as WIN 67721, WIN 12901, WIN 68165, and WIN 68209 or others may be preferred.

In one specific embodiment, the active agent may be a therapeutic agent for prevention and/or treatment of pulmonary disorders. Non-limiting examples of such agents include steroids, beta-agonists, anti-fungal agents, anti-microbial compounds, bronchial dialators, anti-asthmatic agents, non-steroidal anti-inflammatory agents (NSAIDS), AAT, and agents to treat cystic fibrosis. Non-limiting examples of steroids for prevention and/or treatment of pulmonary disorders include but are not limited to beclomethasone (such as beclomethasone dipropionate), fluticasone (such as fluticasone propionate), budesonide, estradiol, fludrocortisone, flucinonide, triamcinolone (such as triamcinolone acetonide), flunisolide, and salts thereof. Non-limiting examples of beta-agonists for prevention and/or treatment of pulmonary disorders include salmeterol xinafoate, formoterol fumarate, levoalbuterol, bambuterol, tulobuterol, and salts thereof. Non-limiting examples of anti-fungal agents for prevention and/or treatment of pulmonary disorders include itraconazole, fluconazole, amphotericin B, and salts thereof.

The active agents may be used in a combination of two or more thereof. Non-limiting exemplary combinations include a steroid and a beta-agonist, e.g., fluticasone propionate and salmeterol, budesonide and formoterol, etc. Many other viable therapeutically active agent combinations are well known to those of ordinary skill in the art.

Non-Volatile Material

Compositions containing the microparticles can contain at least one non-volatile material, the at least one non-volatile material(s) being different in their chemical structures and/or compositions from that of the one or more macromolecules that form the microparticles.

Generally, the non-volatile materials have a boiling point and/or a flash point greater than about 100° C., greater than about 150° C., and/or greater than about 200° C. The non-volatile materials can be natural, synthetic, semi-synthetic, or recombinant. The one or more non-volatile materials are typically nonionic polymers which can be independently hydrophilic, amphiphilic, aqueous-soluble (e.g., water-soluble), and/or aqueous-miscible (e.g., water-miscible), or salts of such nonionic polymers. The one or more non-volatile materials can beneficially independently or collectively reduce the solubility of one or more macromolecules in the continuous phase, or in the one or more fluids therein. The one or more non-volatile materials, when present in the continuous phase, typically do not covalently and/or ionically interact with, or denature, the one or more macromolecules in the microparticles. Additionally, the one or more non-volatile materials, when present in the continuous phase, typically do not complex, conjugate, aggregate, and/or agglomerate with each other, or otherwise come together, such as via covalent, ionic, and/or other interactions. Further, the one or more non-volatile materials in the continuous phase typically do not undergo gelation (e.g., form a hydrogel), either by themselves or with other ingredients present in the continuous phase. The one or more non-volatile materials independently generally have molecular weights greater than or equal to values such as 200 daltons, 300 daltons, 400 daltons, 600 daltons, 800 daltons, 1,000 daltons, 1,500 daltons, 2,000 daltons, 2,500 daltons, 3,000 daltons, 3,500 daltons, 4,000 daltons, 5,000 daltons, 8,000 daltons, and 10,000 daltons, or up to about 3,000 kilodaltons (kd), or in a range between any two of such values, for example, between 200 daltons and 10,000 daltons, between 1000 daltons and 1500 daltons, between 1000 daltons and 2,000 daltons, between 1000 daltons and 2,500 daltons, between 1000 daltons and 3,000 daltons, between 1000 daltons and 3,500 daltons, between 1000 daltons and 4,000 daltons, between 1000 daltons and 5,000 daltons, between 1000 daltons and 8,000 daltons, between 1000 daltons and 10,000 daltons, between 1,500 daltons and 2,000 daltons, between 1,500 daltons and 2,500 daltons, between 1,500 daltons and 3,000 daltons, between 1,500 daltons and 3,500 daltons, between 1,500 daltons and 4,000 daltons, between 1,500 daltons and 5,000 daltons, between 1,500 daltons and 8,000 daltons, between 1,500 daltons and 10,000 daltons, between 2,000 daltons and 2,500 daltons, between 2,000 daltons and 3,000 daltons, between 2,000 daltons and 3,500 daltons, between 2,000 daltons and 4,000 daltons, between 2,000 daltons and 5,000 daltons, between 2,000 daltons and 8,000 daltons, between 2,000 daltons and 10,000 daltons, etc.

Non-limiting examples of non-volatile materials for the continuous phase include the non-ionic water-soluble and/or water-miscible polymers disclosed in U.S. Pat. Nos. 5,525,519, 5,554,730, 5,578,709, 5,599,719, 5,981,719, 6,090,925, 6,268,053, and 6,458,387, U.S. Publication Nos. 20030059474, 20030064033, 20040043077, 20050048127, 20050142201, 20050142205, 20050142206, 20050147687, 20050170005, 20050233945, 20060018971, 20060024240, 20060024379, 20060260777, 20070092452, 20070207210, and 20070281031, the disclosures of which are herein incorporated by reference in their entirety. The non-volatile material(s) are typically non-ionic, and can be hydrophilic, amphiphilic, aqueous-soluble, aqueous-miscible, and/or soluble or miscible in an aqueous-soluble or aqueous-miscible fluid at a temperature of 40° C. or below. Non-limiting examples of suitable non-volatile materials may be linear, branched, or cyclic, and include non-ionic polyethers, non-ionic copolyethers, non-ionic polyesters, non-ionic copolyesters, non-ionic polyether-polyester copolymers, non-ionic vinyl polymers, non-ionic pyrrolidone-containing polymers, non-ionic polymeric carbohydrates, derivatives and salts thereof, and combinations of two or more thereof. Non-limiting examples of non-ionic polyethers and non-ionic copolyethers (including copolymers and terpolymers) include but are not limited to hydroxy-terminated polyethers (e.g., polyether alcohols, polyether polyols, ethylene oxide end-capped polyethers other than polyethylene glycols) and alkyl (e.g., methyl, ethyl, propyl, butyl, etc.) end-capped derivatives thereof, such as polyalkylene glycols (e.g., poly-oxy-1,2-alkylene glycols like polyethylene glycols and polypropylene glycols, as well as polytrimethylene ether glycols and polytetramethylene ether glycols), hydroxy-terminated copolyethers (e.g., copolyether alcohols, copolyether polyols, ethylene oxide end-capped copolyethers) and alkyl (e.g., methyl, ethyl, propyl, butyl, etc.) end-capped derivatives thereof, such as block copolyethers of two or more different 1,2-alkylene oxides (e.g., polyoxyethylene-polyoxypropylene copolymers like poloxamers) and copolyethers of one or more 1,2-alkylene oxides and one or more of tetrahydrofuran, tetrahydropyran, and 1,3-propanediol (e.g., (polyethylene glycol)-(polytrimethylene ether glycol) copolymers, (polyethylene glycol)-(polytetramethylene ether glycol) copolymers). Non-limiting examples of non-ionic polyesters and non-ionic copolyesters (including copolymers and terpolymers) include hydroxy-terminated polyesters (e.g., polyester polyols, copolyester polyols, ethylene oxide end-capped or poly-oxyethylene-terminated polyesters, and certain silicone polyesters, such as the likes of polyoxyethylene glycerin dicarboxylic acid esters, polyoxyethylenesorbitol dicarboxylic acid esters, polyoxyethylene glycol dicarboxylic acid esters, and polyoxyethylenealkyl esters. Non-limiting examples of non-ionic polyether-polyester copolymers (including terpolymers) include but are not limited to block copolymers of one or more lactones and/or dicarboxylic acids and one or more 1,2-alkylene oxides), esterification derivatives of the non-ionic polyethers and non-ionic copolyethers disclosed herein, and etherification derivatives of the non-ionic polyesters and non-ionic copolyesters disclosed herein, such as (polyethylene glycol)-polycaprolactone block copolymers. Non-limiting examples of non-ionic vinyl polymers (including copolymers and terpolymers) and pyrroli-done-containing non-ionic polymers (including copolymers and terpolymers) include but are not limited to polyvinyl alcohols, homopolymers and copolymers (including terpolymers) of hydroxyalkyl(alk)acrylates (e.g., hydroxyethyl acrylate, hydroxypropyl acrylate, hydroxyethyl methacrylate, hydroxypropyl methacrylate), oligo-oxyalkylene(alk) acrylates (e.g., oligo-oxyethylene acrylates, oligo-oxyethylene methacrylates), and/or alkyl end-capped oligo-oxyalkylene (alk)acrylates (e.g., methyl-capped), polyvinylpyrrolines, and (alkenyl pyrrolidone)-containing homopolymers and copolymers.

Non-limiting examples of nonionic polymeric (including oligomeric) carbohydrates (having a molecular weight of 200 daltons to 5,000,000 daltons, such as 1,000 daltons, 3,000 daltons, 5,000 daltons, 10,000 daltons, 30,000 daltons, 50,000 daltons, 100,000 daltons, 300,000 daltons, 500,000 daltons, 1,000,000 daltons, or 3,000,000 daltons, or in a range between any two of such values) and derivatives thereof include but are not limited to starch, amylopectin (branched polysaccharides), amylose (linear polysaccharides), cellulose, guar gum, guar polysaccharides, xanthan gum, dextrins (e.g, cyclodextrins, maltodextrins), dextrans, polydextroses, gellan gum, pullulan, cellodextrins, beta-glucans, and derivatives thereof, for example, nonionic esters formed by esterification, including but not limited to benzoates and alkanoates such as acetates, propionates, butyrates, and hexanoates; or nonionic ethers formed by etherification such as nonionic starch ethers, nonionic amylopectin ethers, nonionic amylose ethers, nonionic cellulose ethers, nonionic guar ethers, nonionic starch esters, nonionic amylopectin esters, nonionic amylose esters, nonionic cellulose esters, nonionic starch ether esters, nonionic starch ester ethers, nonionic cellulose ether esters, and nonionic cellulose ester ethers. Non-limiting examples of nonionic starch ethers include alkylstarches such as methylstarches, ethylstarches, propylstarches, and butyl-starches; hydroxyalkyl starches such as hydroxyethyl starches (e.g., tetrastarch, pentastarch, hetastarch), hydroxypropyl starches, hydroxybutyl starches, and hydroxypentyl starches; as well as alkylhydroxyalkyl starches such as methylhydroxyethyl starches, methylhydroxypropyl starches, and ethylhydroxypropyl starches. Non-limiting examples of non-ionic amylopectin ethers and nonionic amylose ethers include hydroxyethyl amylopectins, hydroxypropyl amylopectins, hydroxyethyl amyloses, and hydroxypropyl amyloses. Non-limiting examples of nonionic cellulose ethers include alkylcelluloses such as methylcelluloses, ethylcelluloses, propylcelluloses, isopropylcelluloses, and butylcelluloses; hydroxyalkyl celluloses such as hydroxyethyl celluloses, hydroxypropyl celluloses, hydroxyisopropyl celluloses, hydroxybutyl celluloses, and hydroxypentyl celluloses; as well as alkylhydroxyalkyl celluloses such as methylhydroxyethyl celluloses, methylhydroxypropyl celluloses, methylhydroxybutyl celluloses, ethylhydroxyethyl celluloses, ethylhydroxypropyl celluloses, propylhydroxyethyl celluloses, propylhydroxypropyl celluloses, isopropylhydroxypropyl celluloses, butylhydroxypropyl celluloses, pentylhydroxypropyl celluloses, and hexylhydroxypropyl celluloses. Non-limiting examples of nonionic guar ethers include alkylguar polysaccharides such as methylguar polysaccharides, ethylguar polysaccharides, propylguar polysaccharides, and butylguar polysaccharides; hydroxyalkylguar polysaccharides such as hydroxyethylguar polysaccharides, and hydroxypropylguar polysaccharides; as well as alkylhydroxyalkylguar polysaccharides such as methylhydroxyethylguar polysaccharides, methylhydroxypropylguar polysaccharides, ethylhydroxypropylguar polysaccharides. Other nonionic polymeric carbohydrates include methyl cellulose, hydroxyethyl cellulose, hydroxyethyl methylcellulose, hydroxypropyl methylcellulose, ethylhydroxyethyl cellulose, methylethylhydroxyethyl cellulose, butylglycidyletherhydroxyethyl cellulose, laurylglycidyletherhydroxyethyl cellulose, hydroxymethylhydroxyethyl cellulose, butylglycidylether modified hydroxyethyl cellulose, methylhydroxyethylcellulose, methylhydroxypropyl cellulose, starch esters (e.g. alkyl succinic anhydride modified starchstarch acetates and starch alkenylsuccinates), cellulose esters (cellulose monobutyrates and monopropionates), cellulose ether esters (hydroxyalkyl cellulose-2-hydroxycarboxylic acid esters), poly(3-hydroxyoxetane)s. Non-limiting examples of nonionic polymeric carbohydrate esters include those having a degree of substitution ranging from 0.5 to 1.0, such as from 0.7 to 0.9, and are water-soluble. Ionic salts of the foregoing materials, if capable of being made, may also be used. For example, water-soluble and/or -miscible salts of polysaccharides such as dextran sulfate, dextrin sulfate, and sodium alginate, can also be used.

Nonsolvent

To enable and/or facilitate the separation of the microparticles from the other components of the composition containing same, or at least the one or more non-volatile materials thereof, one or more non-solvents may be used alone or in combination of two or more thereof. The non-solvent components are selected such that the non-volatile material(s) of the composition are more soluble in and/or miscible with the non-solvent than are the microparticles. As such, the one or more non-solvents may be suitable as differential solubility systems to separate (e.g., extract, wash, exclude, displace, remove) such materials from the microparticles, using non-limiting techniques such as washing (e.g, centrifugal washing), diafiltration, filtration, dialysis, electrophoresis, or a combination thereof.

Generally, the microparticles are substantially insoluble in the non-solvent. More specifically, the microparticles have a solubility in the non-solvent such that no more than 25% by weight of the microparticles are dissolved as the microparticles are dispersed in the non-solvent, for example, less than 20 wt. %, less than 17.5 wt. %, less than 15 wt. %, less than 12.5 wt. %, less than 10 wt. %, less than 7.5 wt. %, less than 5 wt. %, less than 1 wt. %, or a range between two of these values, for example, between 1 wt. % and 25 wt. %, between 5 wt. % and 25 wt. %, between 7.5 wt. % and 25 wt. %, between 10 wt. % and 25 wt. %, between 12.5 wt. % and 25 wt. %, between 15 wt. % and 25 wt. %, between 17.5 wt. % and 25 wt. %, between 20 wt. % and 25 wt. %, etc.

The non-volatile material should be more soluble in the non-solvent than the microparticles. For example, the non-volatile material(s) can have a solubility in the non-solvent of 10% by weight or greater, such as less than, equal to, or greater than values such as 15%, 20%, 25%, 30%, 40%, 50%, 60%, 70%, 80%, 90%, 100%, or in a range between any two of such values. Additionally, the at least one non-volatile material may be entirely miscible with the non-solvent.

The non-solvent or at least the non-aqueous liquid therein generally have an oral $LD_{50}$ in rats greater than 1.6 g/kg by body weight, such as 1.7 g/kg or greater, 1.8 g/kg or greater, 2 g/kg or greater, 2.5 g/kg or greater, 3 g/kg or greater, 4 g/kg or greater, 5 g/kg or greater, or in a range between two of such values. The non-solvent is usually free of any materials having an oral $LD_{50}$ in rats of 1.6 g/kg by body weight or less. Additionally or alternatively, the non-solvent or at least the non-aqueous liquid therein may have a permitted daily exposure to human of 50 mg/day or greater.

The non-solvent generally comprises an aqueous solution including at least one multivalent cation. The multivalent (e.g., divalent, trivalent) cations present in the non-solvent may be selected from multivalent metal cations including but not limited to $Ba^{2+}$, $Ca^{2+}$, $Co^{2+}$, $Cr^{2+}$, $Cu^{2+}$, $Fe^{2+}$, $Mg^{2+}$, $Mn^{2+}$, $Sr^{2+}$, $Zn^{2+}$, $Al^{3+}$, $Fe^{3+}$, and combinations of two or more thereof. The multivalent cation(s) are generally present in the non-solvent at a concentration of 0.01 mM to 50 mM, or even greater, for example, at concentrations such as 0.05 mM, 0.1 mM, 0.2 mM, 0.5 mM, 1 mM, 1.5 mM, 2 mM, 5 mM, 10 mM, 20 mM, 80 mM, 100 mM, or in a range between any two of such values, for example, between 0.01 mM and 100 mM, between 0.01 mM and 80 mM, between 0.01 mM and 20 mM, between 0.01 mM and 10 mM, between 0.01 mM and 5 mM, between 0.01 mM and 2 mM, between 0.01 mM and 1.5 mM, between 0.01 mM and 1 mM, between 0.01 mM and 0.5 mM, between 0.01 mM and 0.2 mM, between 0.01 mM and 0.1 mM, between 0.01 mM and 0.05 mM, etc. Advantageously, non-solvents containing such multivalent cations have been found to reduce the solubility of microparticles in aqueous solution without negatively affecting their activities.

The non-solvent may further contain one or more volatile organic cations. Non-limiting examples of volatile organic cations include ammonium cation, dialkylammonium cations (e.g., dimethylammonium cation), trialkylammonium cations (e.g., trimethylammonium cation), and combinations thereof. In another example, the one or more non-solvents may further contain one or more suitable anions, such as one or more non-multivalent cation-chelating anions. Non-limiting examples of non-chelating anions include acetate, ascorbate, aspartate, bicarbonate, carbonate, chloride, form ate, salicylate, succinate, sulfate, and combinations of two or more thereof. The non-solvent is typically free (e.g., contain less than 0.50 wt. %, less than 0.25 wt. %, and/or 0 wt. %) of chelating agents to the one or more free multivalent cations. Non-limiting examples of such chelating agents include diethyldithiocarbamate (DEDTC), ethylenediaminetetraacetic acid (EDTA), TPEN (N,N,N',N'-Tetrakis(2-pyridylmethyl)ethylenediamine), DMPS (2,3-dimercapto-1-propanesulfonic acid), 1,10-phenanthroline, deferoximine, acacia, citrate, malate, lactate, picolinate, gluconate, glucose, glutathione, histidine, cysteine, phosphate, and Tris buffer.

Typically, the non-solvent is free (e.g., contain less than 0.50 wt. %, less than 0.25 wt. %, and/or 0 wt. %) of organic liquids including but not limited to alcohols, ketones, nitriles, ethers, alkanes, and the like. The non-solvent may advantageously be pharmaceutically acceptable (e.g., and thus such non-solvents can also be used as a diluent for injection or other route of administration for human subjects after microparticles are transferred into same).

The non-solvent may have a pH above the surface neutral point of the microparticles such that, when it is combined with a composition comprising a plurality of solid microparticles to form a mixture containing one or more liquid phases and the solid microparticles, the liquid phase of said mixture (or more generally, the mixture or suspension itself) has a pH in excess of the surface neutral point of the microparticle. Similarly, when used in connection with microparticles containing one or more bioactive macromolecules, the non-solvent can have a pH above the isoelectric point of the bioactive macromolecule such that, when it is combined with the composition comprising a plurality of solid microparticles to form a mixture containing one or more liquid phases and the solid microparticles, any resulting liquid phase (or more generally, the mixture itself) has a pH in excess of the isoelectric point of the bioactive molecule therein. Thus, the non-solvent may contain a pH adjusting agent such as a base or a buffer in addition to the multivalent cation. As is known to those skilled in the art, the surface neutral point of a particle and the isoelectric point of any particular macromolecule may easily be determined using routine methods, for example, those disclosed in U.S. Patent Publication No. 20060260777. Typically, the pH of the mixture is at least 0.3 pH units greater, for example, at least 0.5, at least 0.8, and/or at least 1 pH units greater than the surface neutral point of the microparticles and/or the isoelectric point of the macromolecule contained therein. Non-solvents having a pH greater than 7, such as equal to or greater than 7.3, 7.5, 7.8, 8, 8.5, 9, or in a range between any two of such values are typically suitable for use in the methods of the invention.

Exposing the Composition to the Non-Solvent and Removing the Non-Volatile Material When the composition is combined with and/or otherwise exposed to the non-solvent, the physical and/or chemical characteristics of the non-solvent allow the at least one or more non-volatile materials in the composition to be solvated by the non-solvent while keeping the microparticles intact (as the microparticles are less soluble than the non-volatile material in the non-solvent). By removing the resulting liquid phases, the microparticles can be effectively separated from the one or more non-volatile materials and in some instances from one or more other components of the original composition. Non-limiting representative techniques useful to remove portions of the liquid phases and/or otherwise separate the microparticles from the composition or one or more components thereof include washing, filtration (including ultrafiltration), dialysis, diafiltration, phase separation (e.g., centrifugation), electrophoresis, and magnetic extraction, and combinations of two or more thereof. Centrifugation further includes ultracentrifugation, continuous flow centrifugation, and repeated centrifugal washing, and can be performed optionally in combination with liquid removal methods including but not limited to decantation and aspiration.

Certain components of the composition can be removed by selected techniques. For example, the one or more non-volatile materials of the composition can be substantially removed following one, two, or more repeated washings (e.g., by repeated centrifugal washing or repeated diafiltration) using the non-solvent, for example, typically at least 50%, such as 80%, 90%, 95%, 98%, 99%, or greater (e.g., 100%) of the non-volatile material can be removed. Additionally, water and/or other lyophilizable components in the composition, when present, can be removed partially or completely using lyophilization.

The process to separate the microparticles from the composition (or at least a portion of the non-volatile material) therein is typically carried out at a temperature above the freezing temperature of the composition or any component therein (or the continuous phase when a dispersion is being processed), and below the degradation temperature of the microparticles or the bioactive macromolecule therein, such as at or below ambient temperature, or above, at, or below temperatures such as 40° C., 37° C., 30° C., 25° C., 20° C., 15° C., 10° C., 5° C., 2° C., 0° C., −5° C., −10° C., −15° C., −20° C., or in a range between any two of such temperatures.

The processing method may involve utilizing a second non-solvent in which the microparticles are substantially insoluble but which is different from the first non-solvent in one or more of the following (but otherwise the same): (1) pH, (2) ionic strength, and (3) concentration of the free multivalent cation. For example, the second non-solvent may have one or more of the following relative to (but otherwise the same as) the first non-solvent: (1) a higher pH, (2) a lower ionic strength, and (3) a lower concentration of the one or more free multivalent cations. In another example, the second non-solvent may be free of the one or more free multivalent cations in the first non-solvent. In another example, the dispersion processing method may further involve: providing a third non-solvent in which the microparticles are substantially insoluble, wherein the third non-solvent is different from the second non-solvent in one or more of the following: (1) pH, (2) ionic strength, and (3) concentration of the one or more free multivalent cations. Concentrations of buffer salts, if present in the nonsolvents, may also vary.

In one example, at a temperature at or below ambient temperature (such as 2-8° C.), the composition is a dispersion and is subjected to a diafiltration-based concentration process using a non-solvent as the diafiltration medium to exchange with and thereby remove at least a portion of the one or more components of the continuous phase (including the non-volatile material(s) and/or the solvent). Accordingly, the volume of the continuous phase may be reduced to concentrate the microparticles before drying (such as by lyophilization or air drying) is carried out, thereby reducing processing time and cost. A diafilatration apparatus containing a peristaltic pump, a reservoir vessel, a hollow fiber cartridge, and tubing, as known to one of ordinary skill in the art, may be used for the concentration process. Centrifugal washing can be used similarly.

As a non-limiting result of removing one or more components of the continuous phase, an intermediate dispersion containing the microparticles and the non-solvent may be formed through the concentration process, wherein the concentration of the microparticles therein may be elevated many fold (such as 2 fold or more, 5 fold or more, 10 fold or more, 20 fold or more, or 40 fold or more) relative to that of the original dispersion, to 1 g/mL or greater, such as 10 mg/mL or greater. The one or more non-volatile materials (e.g., nonionic polymers) in the original continuous phase may be partially or completely removed during this concentration process. Thus, the continuous phase of the new dispersion may be different from that of the original dispersion in that it is at least substantially free of the one or more non-volatile materials therein. For example, the continuous phase of the new dispersion can contain less than 5% by weight or volume of the one or more non-volatile materials therein, such as less than, or equal to values such as 3%, 2%, 1%, 0.5%, or be present in a range between any two of such values after conducting one or more of the foregoing steps. The microparticles can be suspended freely in the new dispersion, or can be in the form of one or more re-suspendable aggregates (such as isopycnic bands or solid pellets).

The concentrated intermediate dispersion may then be processed using techniques such as dilution and/or repeated centrifugal washing using the same non-solvent that forms the intermediate dispersion or a different non-solvent (such as those disclosed herein) to further remove the one or more non-volatile materials (e.g., nonionic polymers), if any remain present. The separation process may result in a new dispersion containing the microparticles and the non-solvent used during the separation process, with a concentration of the microparticles in a range of 1 mg/mL to 50 g/mL, such as 5 g/mL to 20 g/mL, for example, about 10 g/mL. This new suspension may be stored and/or used as is, or optionally further processed to remove the non-solvent and yield the microparticles in a dry powder form. Non-limiting techniques to remove the non-solvent include various drying techniques (e.g., air drying, lyophilization, freeze-drying, liquid-phase drying, spray drying such as cold spray drying, cryogenic drying, spray-freeze drying, supercritical drying such as supercritical fluid drying, fluidized bed drying), and combinations of two or more thereof.

In one example, a flowable dispersion (e.g., a suspension) containing a plurality of microparticles, such as solid microspheres, is dispersed in a continuous phase containing water or an aqueous solution (such as a buffer solution, optionally with one or more polyvalent cations) with one or more non-volatile materials (e.g., nonionic polymers) solubilized therein. Optionally, the dispersion may be frozen at a temperature of −20° C. or less, preferably −40° C. or less, such as about −60° C., and lyophilized over a sufficient period of time (such as one day or longer, preferably 3 days) to remove substantially all of the water and any other lyophilizable substances to provide a solid dispersion (e.g., lyophilized cake) in which the microparticles may be dispersed in a solid continuous phase of the one or more non-volatile materials. Both the original flowable dispersion and the solid dispersion may be exposed to one or more non-solvents of the present disclosure such as by combining the microparticles with the non-solvent followed with agitation such that the microparticles may be dispersed in a single liquid phase containing the non-solvent (optionally, further containing a portion or all of the continuous phase of the original flowable dispersion). The one or more non-volatile materials may be dissolved or otherwise solubilized in the non-solvent while the microparticles remain dispersed as a solid phase. The new dispersion may be subjected to centrifugation with the supernatant aspirated or decanted away, thereby removing at least a portion of the one or more non-volatile materials solubilized therein from the microparticles. The microparticles may optionally be centrifugally washed more than once with the same non-solvent or with one or more different non-solvents when desired. Any residual non-solvents in the retained microparticles may be removed by drying the microparticles using one or more drying means known to one of ordinary skill in the art (e.g., under nitrogen stream or vacuum).

As previously described, the physical and/or chemical properties of the one or more non-solvents may be chosen such that it is relatively simple, convenient, and/or cost-effective to remove the remainder of the one or more non-solvents from the microparticle (e.g., through lyophilization, diafiltration, air-drying, or combinations thereof) to yield, for example, a dry powder of the microparticles. Alternatively or in addition, the non-solvent may be suitable as a carrier for the intended storage and/or end uses of the microparticles, thus rendering removal unnecessary or only partial removal desirable.

Continuous Phase

The continuous phase of a multi-phasic dispersion processed in accordance with the disclosed methods may be non-solid, for example, containing one fluid or a mixture of two or more fluids (e.g., a homogeneous mixture of two or more liquids wherein at least a first liquid may be soluble in or miscible with at least a second liquid). Non-limiting examples of suitable fluids include aqueous fluids (e.g., water $H_2O$, $D_2O$, aqueous buffers, and other aqueous solutions), non-aqueous fluids (e.g., organic fluids, organic buffers), and combinations of two or more of the foregoing. In one aspect, the non-solid continuous phase may be substantially aqueous, for example, containing more than 10% by volume, such as 25% or more, 50% or more, or 75%, or more water. The continuous phase may be partially or completely aqueous or aqueous-miscible, aqueous-immiscible, water-soluble, or water-insoluble.

When measured at the same ambient temperature, such as 20° C. or 25° C., the continuous phase or the at least one liquid therein typically have density similar or equal to, or less than that of the dispersed phase or the microparticles therein. Most typically, the continuous phase or the at least one liquid therein have a density less than that of the microparticles. For example, the continuous phase or the at least one liquid therein may have a density at ambient temperature that is less than or equal to values such as 1.10 $g/cm^3$, 1.05 $g/cm^3$, 1.0 $g/cm^3$, 0.95 $g/cm^3$, 0.9 $g/cm^3$, 0.8 $g/cm^3$, 0.7 $g/cm^3$, 0.6 $g/cm^3$, or in a range between any two of such values.

The continuous phase may further contain one or more ingredients solubilized therein which are often not substantially incorporated into the microparticles including but not limited to the non-volatile material(s), salts, ions, excess reagents, excipients (e.g., sugars, polyols, surfactants), and/or manufacturing-related compounds. It should be noted, however, that the non-volatile material may be present on/in the dispersed phase, too, for example, the non-volatile material may be trapped within pores of the microparticles and/or otherwise associated with the microparticles. Additionally, these ingredients can be used in the non-solvent described herein. Non-limiting examples of salts include ammonium acetate, ammonium bicarbonate, and other buffer salts known to one of ordinary skill in the art. Non-limiting examples of sugars include trehalose, sucrose, lactose, and other carbohydrates known to one of ordinary skill in the art. Non-limiting examples of polyols include mannitol and other sugar alcohols known to one of ordinary skill in the art. The one or more fluids and/or solutes of the continuous phase may be, independently, partially or fully aqueous-miscible, aqueous-immiscible, water-soluble, and/or water-insoluble.

Dispersed Phase

The dispersed phase of a multi-phasic dispersion processed in accordance with the disclosed methods may comprise solid microparticles. Typically, it is preferred that the microparticles are substantially insoluble in and/or substantially immiscible with the non-solvent, for example, having a solubility therein at ambient temperature of less than 10% by weight, such as 5 wt. % or less, 3 wt. % or less, 1 wt. % or less, 0.5 wt. % or less, 0.1 wt. % or less, 0.05 wt. % or less, 0.01 wt. % or less, or in a range between any two of such values.

The dispersed phase may further include other materials in association with the solid microparticles, for example, a non-volatile material, salt, or excipient added during microparticle formation. Generally, such materials are not desired in the isolated microparticles and are therefore desirably removed from the dispersion. Accordingly, it is desirable for such materials to have relatively higher solubilities in the non-solvent described above.

The following examples are provided to illustrate the invention, but not to limit the scope thereof.

Example 1

A bioactive macromolecule solution of a polyclonal antibody (2.1 mg/mL intravenous immunoglobulin IVIG in 100 mM ammonium acetate buffer at pH 5.8) and a solution containing a nonvolatile material (24% poloxamer 188 in 100 mM ammonium acetate buffer at pH 5.8) were pre-heated to 50° C. or lower (e.g., 48° C., 45° C.) and mixed at a volume ratio of 1:1. The transparent mixture (1.2 mg/mL IVIG, 12% poloxamer 188, 100 mM ammonium acetate, pH 5.8) was then cooled to between 0-5° C. (placed in a −20° C. freezer for 10 min to reach 4° C. or 2° C., but no frozen) to form a 1 mg/mL IVIG microsphere suspension. An aliquot of the IVIG microsphere suspension was mixed with a first washing solution (12% poloxamer 188, 300 mM sodium salicylate, 48 mM zinc sulfate, pH unadjusted, cooled to about 4° C.) at a volume ratio of 1:1. The mixed suspension was centrifuged at 4° C. such that the microspheres formed a pellet. The supernatant was decanted, and the microsphere pellet was re-suspended in a volume of a second washing solution (400 mM sodium salicylate, 48 mM zinc sulfate). The morphology of the IVIG microspheres in the re-suspension was confirmed using light microscopy to be the same as that of the IVIG microspheres in the original suspension.

Example 2

A bioactive macromolecule solution of a polyclonal antibody (2.1 mg/mL IVIG in 100 mM ammonium acetate buffer at pH 5.8) was prepared by dialyzing a 10% solution of IVIG against 100 mM ammonium acetate buffer (pH 5.8) at 4° C. overnight. The macromolecule solution and a polymer solution (24% poloxamer 188 in 100 mM ammonium acetate buffer at pH 5.8) were pre-heated (warm water bath) to 50° C., and mixed at a volume ratio of 1:1. The transparent mixture was then cooled to about 4° C. to form a 1 mg/mL IVIG microsphere suspension. At a volume ratio of 1:1, three aliquots of the IVIG microsphere suspension were separately mixed with three nonsolvents (2 mM zinc acetate, 100 mM ammonium acetate) of pH 7.3, 7.5, and 7.8, respectively. The mixed suspensions were centrifuged at 3,000 rpm and at 4° C. for 5 min. The supernatants were removed, and the microsphere pellets were centrifugally washed with the same respective nonsolvents two more times. The resulting microsphere pellets were centrifugally washed twice with 6 mL, and then re-suspended in 3 mL, of a buffer solution (0.2 mM ammonium acetate, pH 8.05). Measurements of protein concentration (OD280) of the supernatants from each wash step demonstrated increased up to 18% of the microspheres dissolved in solution. It is believed that washing at lower temperatures will significantly reduce the amount of dissolution. Integrity studies were also conducted by dissolving the washed microspheres in PBS, and analyzing the solutions by HPLC using PBS as the running buffer. Monomer contents of the solutions were greater than 90% for each of the three different nonsolvents, and were greater in each instance than the starting material itself, indicating that substantially no degradation (e.g., dimer formation) to the bioactive macromolecule occurred as a result of the washing process.

Example 3

A bioactive macromolecule solution of a polyclonal antibody (2.8 mg/mL IVIG in 100 mM sodium acetate buffer at pH 5.2) and a solution of a nonvolatile material (28% PEG 3350 in 100 mM sodium acetate buffer at pH 5.2) were pre-heated (warm water bath) to 45° C., and mixed at a volume ratio of 1:1. The transparent mixture was then cooled to about 4° C. to form a 1.4 mg/mL IVIG microsphere suspension. At 4° C., aliquots of the IVIG microsphere suspension were separately and repeatedly washed centrifugally with various nonsolvents each containing zinc acetate at 2 mM, ammonium acetate at 10 mM to 250 mM, and ranging in pH from 6.5 to 8.5. The collected IVIG microsphere pellets were then separately and repeatedly washed centrifugally with various second nonsolvents each containing zinc acetate at 0.2 mM, ammonium acetate at 10 mM to 250 mM, and ranging in pH from 6.5 to 8.5. The collected IVIG microsphere pellets were then re-suspended in the second nonsolvents or lyophilized.

Example 4

A bioactive macromolecule solution of a monoclonal antibody (2 mg/mL anti factor VIII antibody, anti-FVIII, in 100 mM ammonium acetate buffer at pH 5.8) was obtained by dialyzing a PBS solution of the antibody (pH 7.1, Baxter Hayward) against 100 mM ammonium acetate buffer (pH 5.8) at 4° C. for 2 days. A solution of a nonvolatile material (24% poloxamer 188 in 100 mM ammonium acetate buffer at pH 5.8) was pre-heated (warm water bath) to 45° C. The macromolecule and polymer solutions were gently mixed (using inversion) at a volume ratio of 1:1. The transparent mixture was equilibrated (warm water bath) at 45° C. and then cooled to about 2-4° C. (but not frozen) to form a 1 mg/mL anti-FVIII microsphere suspension. Separate aliquots of the microsphere suspension were centrifugally washed 3 times with the a first nonsolvent and twice with a second nonsolvent according to the table below, and microspheres were collected and lyophilized.

| Samples | First washing solution | Second washing solution |
|---|---|---|
| Sample A | Buffer A | Buffer C |
| Sample B | Buffer A | Buffer D |
| Sample C | Buffer B | Buffer C |
| Sample D | Buffer B | Buffer D |

Buffer A - 2 mM zinc acetate, 100 mM ammonium acetate, pH 7.5
Buffer B - 2 mM zinc acetate, 100 mM ammonium acetate, pH 8.0
Buffer C - 0.2 mM zinc acetate, 10 mM ammonium acetate, pH 8.0
Buffer D - 0.2 mM zinc acetate, 10 mM ammonium acetate, pH 8.8

Integrity studies were conducted by dissolving the washed microspheres in PBS, and analyzing the solutions by HPLC and by measuring binding activity by ELISA. Both experiments showed similar profiles to control microspheres washed with distilled water (pH 10.2 with ammonium acetate) and a 60:40 mixture of tert-butyl alcohol and water.

Example 5

A macromolecule solution (2 mg/mL anti-FVIII in 200 mM sodium acetate buffer at pH 5.5) and a solution of a nonvolatile material (24% PEG 3350 in 100 mM sodium acetate buffer at pH 5.2) were pre-heated (warm water bath) to 45° C., and mixed at a volume ratio of 1:1. The transparent mixture was then cooled to about 4° C. to form a 1 mg/mL anti-FVIII microsphere suspension. At 4° C., aliquots of the anti-FVIII microsphere suspension were separately diafiltered against different nonsolvents at various multiples of the volume of the aliquots, each of the first washing solutions containing zinc acetate at 2 mM, ammonium acetate at 10 mM to 250 mM, and pH's ranging from 6.5 to 8.5. The resulting intermediate anti-FVIII microsphere suspensions were then separately diafiltered against different second nonsolvents at various multiples of the volume of the intermediate suspensions, each of the second washing solutions containing zinc acetate at 0.2 mM, ammonium acetate at 10 mM to 250 mM, and pH ranging from 6.5 to 8.5. The resulting final anti-FVIII microsphere suspensions were separately concentrated and lyophilized.

Example 6

In this prophetic example, 25 mL of a macromolecule solution (8 mg/mL monoclonal antibody in 50 mM ammonium acetate buffer at pH 5.8) and 15 mL of a nonvolatile material solution (29% PEG 3350 in 50 mM sodium acetate buffer at pH 5.8) are pre-heated (warm water bath) to a temperature between 40° C. and 50° C. (e.g., 45° C.), and mixed. The transparent mixture (5 mg/mL monoclonal antibody, 11% PEG 3350, 50 mM ammonium acetate, pH 5.8) is then cooled to about 4° C. over 1 hour to form a 5 mg/mL monoclonal antibody microsphere suspension. At or below ambient temperature (e.g., 4° C.), the monoclonal microsphere suspension is quenched with an equal volume of a first nonsolvent (2 mM zinc acetate, 250 mM ammonium acetate, pH 7.5) and then concentrated to 10 mL using diafiltration. The concentrated microsphere suspension is diafiltered against 3 volume exchanges (10 mL each) of a second nonsolvent (2 mM copper acetate, 100 mM ammonium acetate, pH 7.5) and then 3 volume exchanges (10 mL each) of a third washing buffer (2 mM iron (II) acetate, 25 mM ammonium acetate, pH 7.5). The resulting microsphere suspension is charged with 0.2 mL of 8% sucrose solution (as stabilizer) and lyophilized.

Example 7

In this prophetic example, a macromolecule solution (1-40 mg/mL macromolecule in a reaction buffer containing 10-2000 mM buffer salt at pH less than 7) and a solution of a nonvolatile material (10-50% nonionic polymer in the same reaction buffer of the macromolecule solution) are pre-heated (warm water bath) to a temperature between 40° C. and 50° C. or higher (less than 100° C.), and mixed. The transparent mixture is then cooled to 10° C. or below but not frozen to form a macromolecule microsphere suspension. At or below ambient temperature but above the freezing temperature of the microsphere suspension, the microsphere suspension is washed (e.g., via centrifugation and/or diafiltration, among other means) with at least a first nonsolvent (containing 1-2000 mM of a free multivalent metal cation such as zinc cation and having a pH greater than about 6, and optionally further containing 10-250 mM of a volatile organic cation such as ammonium cation and/or 10 mM or greater of a nonchelating anion such as acetate). The product of the washing (e.g., pellet, filtrate, suspension) is optionally washed with a second nonsolvent, a third nonsolvent, or more nonsolvent that are different from the first nonsolvent in one or more of the following: (1) concentration of the free multivalent metal cation, (2) concentration of the volatile organic cation, if present, (3) concentration of the nonchelating anion, if present, (4) pH, and (5) ionic strength. At the end of all the washes, one or more stabilizers (e.g., sugars, surfactants, salts, polyols) can optionally be added to the collected microspheres, and the microspheres can either be re-suspended in one of the nonsolvents, or lyophilized into a dry powder, for storage and/or end use (e.g., administration into a human subject).

Any nucleic acid including but not limited to antisense nucleic acids and siRNAs can be used as the macromolecule. Exemplary antisense oligodeoxynucleotides (anti-CD40, anti-CD80, anti-CD86) for use as the macromolecule are commercially available in HPLC-purified lyophilized preparations. These oligonucleotides are phosphorothioated in the oligonucleotide backbone and are available from Integrated DNA Technologies, (Coralville, Iowa). Exemplary siRNA molecules are made up of unmodified duplexes optionally having one strand labeled with a fluorescent dye. HPLC-purified and lyophilized preparations of suitable siRNA molecules are commercially available from Dharmacon (Dharmacon, Lafayette, Colo.).

Numerous modifications and variations of the invention are expected to occur to those skilled in the art in view of the accompanying disclosure. Consequently only such limitations as appear in the appended claims should be placed on the invention.

What is claimed is:

1. A method of processing microparticles comprising:
providing a composition comprising a plurality of solid microparticles and at least one non-volatile material;
providing a non-solvent comprising an aqueous solution containing at least one free multivalent cation;
exposing the composition to the non-solvent to form a mixture containing one or more liquid phases and the solid microparticles; and
removing at least a portion of the one or more liquid phases while retaining at least the microparticles, thereby removing at least a portion of the non-volatile material from the composition,
wherein the non-volatile material is more soluble in the non-solvent than are the microparticles,
wherein the non-volatile material comprises a non-ionic aqueous-soluble polymer or a non-ionic aqueous-miscible polymer,
wherein the solid microparticles comprise at least one bioactive macromolecule that is an antibody,
wherein the activity of the bioactive macromolecule remains substantially the same before and after the exposing and removing steps, and
wherein the solid microparticles have a diameter of less than 1 mm.

2. The method of claim 1, wherein the non-volatile material is soluble in the non-solvent.

3. The method of claim 1, wherein the solid microparticles are substantially insoluble in the non-solvent.

4. The method of claim 3, wherein the solid microparticles have less than 20 weight percent (wt. %) solubility in the non-solvent.

5. The method of claim 1, wherein the solid microparticles have less than 20 wt. % solubility in the non-solvent and are more soluble in an aqueous solution that is the same as the non-solvent but is free of the free multivalent cation.

6. The method of claim 1, wherein exposing and/or removing steps comprise centrifugal washing, diafiltration, filtration, dialysis, electrophoresis, or a combination thereof.

7. The method of claim 1, wherein the non-solvent is free of chelating agents to the multivalent cation.

8. The method of claim 1, wherein the multivalent cation is selected from the group consisting of $Ba^{2+}$, $Ca^{2+}$, $Co^{2+}$, $Cr^{2+}$, $Cu^{2+}$, $Fe^{2+}$, $Mg^{2+}$, $Mn^{2+}$, $Sr^{2+}$, $Zn^{2+}$, $Al^{3+}$, $Fe^{3+}$, and combinations thereof.

9. The method of claim 1, wherein the multivalent cation is present in the non-solvent at a concentration of 0.01 mM to 50 mM.

10. The method of claim 1, wherein the multivalent cation is present in the non-solvent at a concentration of 0.2 mM to 2 mM.

11. The method of claim 1, wherein the non-solvent further comprises one or more non-chelating anions selected from the group consisting of acetate, ascorbate, aspartate, bicarbonate, carbonate, chloride, formate, salicylate, succinate, sulfate, and combinations of two or more thereof.

12. The method of claim 1, wherein the bioactive macromolecule is selected from polycolonal antibodies and monoclonal antibodies.

13. The method of claim 1, wherein the solid microparticles comprise the bioactive macromolecule at least on an outer surface of the solid microparticle.

14. The method of claim 1, wherein the non-volatile material is selected from the group consisting of nonionic polyethers, nonionic copolyethers, nonionic polyesters, nonionic copolyesters, nonionic polyether-polyester copolymers, starch, cellulose, guar gum, nonionic starch ethers, nonionic cellulose ethers, nonionic guar ethers, nonionic starch esters, nonionic cellulose esters, nonionic starch etheresters, nonionic cellulose etheresters, nonionic vinyl polymers, ionic salts thereof, and combinations thereof.

15. The method of claim 1, wherein the microparticles comprise a carrier macromolecule.

16. The method of claim 1, wherein the microparticles are amorphous, spherical, or both.

17. The method of claim 1, wherein exposing comprises combining the non-solvent and the composition to form a mixture having a single aqueous liquid phase.

18. The method of claim 1, further comprising isolating the microparticles.

19. The method of claim 18, further comprising drying the isolated microparticles into a powder.

20. The method according to claim 19, wherein drying comprises lyophilizing the microparticles.

21. The method according to claim 1, wherein the composition is a multi-phasic dispersion comprising dispersed and continuous phases, the dispersion comprising the solid microparticles and at least one of a non-volatile material and a solvent.

22. The method according to claim 1, wherein the multivalent cation comprises $Zn^{2+}$.

* * * * *

UNITED STATES PATENT AND TRADEMARK OFFICE
CERTIFICATE OF CORRECTION

| | |
|---|---|
| PATENT NO. | : 8,367,427 B2 |
| APPLICATION NO. | : 12/195092 |
| DATED | : February 5, 2013 |
| INVENTOR(S) | : Darvari |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 692 days.

Signed and Sealed this
Eleventh Day of November, 2014

Michelle K. Lee
*Deputy Director of the United States Patent and Trademark Office*